(12) United States Patent
Guo

(10) Patent No.: US 10,678,505 B2
(45) Date of Patent: Jun. 9, 2020

(54) SUBSET ENCODING METHOD: INCREASING PATTERN DENSITY FOR FINITE AUTOMATA

(71) Applicant: UNIVERSITY OF VIRGINIA PATENT FOUNDATION, Charlottesville, VA (US)

(72) Inventor: Deyuan Guo, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 1186 days.

(21) Appl. No.: 14/986,131

(22) Filed: Dec. 31, 2015

(65) Prior Publication Data
US 2017/0103333 A1    Apr. 13, 2017

Related U.S. Application Data

(60) Provisional application No. 62/238,864, filed on Oct. 8, 2015.

(51) Int. Cl.
*G06N 5/04* (2006.01)
*G06F 5/01* (2006.01)
*G06F 7/00* (2006.01)
*G16B 99/00* (2019.01)

(52) U.S. Cl.
CPC ............... *G06F 5/01* (2013.01); *G06F 7/00* (2013.01); *G16B 99/00* (2019.02); *G06N 5/04* (2013.01)

(58) Field of Classification Search
None
See application file for complete search history.

(56) References Cited

PUBLICATIONS

Vo, Designing a Parallel Dataflow Architecture for Streaming Large-Scale Visualization on Heterogeneous Platforms, Doctoral Thesis, University of Utah, (2011) pp. 1-131 (Year: 2011).*
Dlugosch Paul et al., "An Efficient and Scalable Semiconductor Architecture for Parallel Automata Processing", IEEE Transactions on Parallel and Distributed Systems, 2014, No. 12, pp. 1-11; Cited in the Specification.
(Continued)

*Primary Examiner* — Wilbert L Starks
(74) *Attorney, Agent, or Firm* — Westerman, Hattori, Daniels & Adrian, LLP

(57) ABSTRACT

The subset encoding method and related automata designs for improving the space efficiency for many applications on the Automata Processor (AP) are presented. The method is a general method that can take advantage of the character-or ability of STEs (State Transition Elements) on the AP, and can relieve the problems of limited hardware capacity and inefficient routing. Experimental results show that after applying the subset encoding method on Hamming distance automata, up to 3.2× more patterns can be placed on the AP if a sliding window is required. If a sliding window is not required, up to 192× more patterns can be placed on the AP. For a Levenshtein distance, the subset encoding can split the Levenshtein automata into small chunks and make them routable on the AP. The impact of the subset encoding method depends on the character size of the AP.

15 Claims, 20 Drawing Sheets
Specification includes a Sequence Listing.

(56) References Cited

PUBLICATIONS

Roy Indranil et al., "Finding Motifs in Biological Sequences using the Micron Automata Processor", IEEE 28th International Parallel and Distributed Processing Symposium, May 2014, pp. 415-424; Cited in the Specification.
Zhou, Keira et al., "Brill Tagging using the Micron Automata Processor", IEEE ICSC, Feb. 2015, 8 pages; Cited in the Specification.
Wang, Ke et al., "Association Rule Mining with the Micron Automata Processor", IEEE IPDPS May 2015, 10 pages; Cited in the Specification.
Bo, Chunkun et al., "Entity Resolution Acceleration using Micron's Automata Processor", ASBD workshop with ISCA, Jun. 2015, 4 pages; Cited in the Specification.
Tracy II, Tommy et al., "Nondeterministic Finite Automata in Hardware—the Case of the Levenshtein Automaton", ASBD workshop, with ISCA, Jun. 2015, 6 pages; Cited in the Specification.
Becchi, Michela, "Data structures, Algorithms and Architectures for Efficient Regular Expression Evaluation", Washington University, Department of Computer Science and Engineering, 2009, 194 pages; Cited in the Specification.
Even, Shimon et al., "The Complexity of Promise Problems with Applications to Public-Key Cryptography", Information and Control, 1984, vol. 61, No. 2, pp. 159-173; Cited in the Specification.
Prufer, Kay et al., "PatMaN: rapid alignment of short sequences to large databases", Bioinformatics, 2008, vol. 24, No. 13, 1530-1532 pages; Cited in the Specification.
Langmead, Ben et al., "Ultrafast and memory-efficient alignment of short DNA sequences to the human genome", Genome Biology, 2009, vol. 10, No. 3, 10 pages; Cited in the Specification.

* cited by examiner

An input string with a transposition

Patterns:

SUBSET ENCODING METHOD: INCREASING PATTERN DENSITY FOR FINITE AUTOMATA

RELATED APPLICATION

This application claims priority to U.S. Provisional Application No. 62/238,864, "Subset Encoding Method," filed Oct. 8, 2015, which application is incorporated by reference herein in its entirety.

GOVERNMENT INTEREST

This invention was made with government support under Grant No. HR0011-13-3-0002 awarded by the Department of Defense/Defense Advanced Research Projects Agency (DARPA). The government has certain rights in the invention.

BACKGROUND

Micron's Automata Processor (AP) (Document 1) is an innovative hardware accelerator for parallel finite automata-based regular expression matching. It is a non-von Neumann processor, which simulates nondeterministic finite automata (NFAs) mixed with Boolean logic gates and counters. The AP achieves this end by utilizing a bit-parallel technique (Document 2) within DRAM (Dynamic Random Access Memory), allowing it to run many NFAs in parallel.

The memory-derived AP can match an input byte stream with a large number of homogeneous-NFAs (Document 1) on the AP in parallel. Homogeneous-NFAs are computationally equivalent to traditional NFAs, the only difference being that homogeneous-NFAs match characters in states instead of on transitions, as shown in FIG. 1. Each NFA state (called a state transition element, or STE) in the current design of the AP is realized as a 256-bit memory column to represent the subset of 8-bit characters which that state matches. An STE matches on an input character when the input belongs to that state's character subset. This action intuitively operates as a character-OR in regular expressions.

Many automata designs on the AP have been developed for accelerating real-world applications, including: network intrusion prevention (Document 1), DNA motif searching (Document 3), Brill tagging in natural language processing (Document 4), association rule mining (Document 5), entity resolution (Document 6), and DNA alignment (Document 7). These prior works observe the AP achieve more than 100× speedup over CPU implementations.

While working toward these exciting results and other failed ones, it has been found that many automata designs on the AP face a few common problems. One problem is the number of patterns that can be represented on the AP at one time and thus checked concurrently. This pattern density is constrained by hardware resources, such as limited STE capacity or inefficient routing. Hardware limitations on the number of states that an automaton may have can either limit the amount of parallelism that machine is available (making the application less efficient), or prevent an automaton from fitting on the AP altogether (making the application impossible to accelerate with the AP). Additionally, even some small automata may have a complicated transition topology, making them difficult to route on the architecture. This can cause a poor STE utilization rate. As a consequence, for large problems that exceed the capacity of the AP, one may have to either use more AP hardware, or perform the computation using many passes through the input stream.

Another problem is that it is difficult to fully utilize the powerful character-OR ability of STEs on the AP. One reason is that if many regular expression patterns are combined together using character-ORs, one cannot later distinguish which character was matched. The other reason is that there is a mismatch between common regular expression structures and the matching procedure of the AP, as real world regular expressions typically operate over unions of larger subexpressions rather than using single character-ORs.

It is observed that it is possible to overcome these limitations. Since each STE is a 256-bit memory column, it can represent any one of $2^{256}$ possible subsets of 8-bit characters. This gives plenty of entropy to represent more complex matching behavior than the simple character-OR.

To address these problems, the subset encoding method, which can help the AP to achieve better utilization of its hardware resources for various applications, is proposed. The subset encoding method encodes both application data and patterns into subsets of characters, illustrated in FIG. 2. For example, it can encode a 64-character DNA sequence into a subset of 8-bit characters, so that it only uses one STE to represent this DNA sequence. By matching encoded data with encoded automata, a richer design space can be accessed, addressing those problems mentioned above.

The subset encoding method can fully exploit the character-OR ability of STEs by encoding a sequence of data into a subset of characters, which are then put in a single self-loop STE. Effectively, the subset encoding method encapsulates a short transition history using only one STE, allowing that STE to match on a sequence of characters rather than being limited to matching on just one character. From here, the method can be adapted to find solutions, which best fit the characteristics of individual applications by analyzing tradeoffs among input stride, input rate, and alphabet size.

Furthermore, the subset encoding method improves the space efficiency and the degree of parallelism. This results in smaller automata structures with fewer states and connections, enabling more automata to be placed on the AP by reducing routing complexity. For example, the subset encoding is applied to traditional Hamming distance automata and Levenshtein automata. The large structures required for these automata make it very difficult or sometimes impossible to place and route on the AP. It is shown that after applying the subset encoding method, the automata structures become highly compressed and thus, require significantly fewer routing resources on the AP.

Experimental results show that by applying the subset encoding method, the space efficiency of these automata can be improved from 3× to 192× for different application scenarios. Multiple-stride in the subset encoding can be used to increase the input rate. As a result, overall performance on the AP can be significantly improved. This encoding technique will impact future decisions in the design of the AP or other automata-based co-processors.

Related Works

The input stride technique was discussed in Becchi's Ph.D. thesis (Document 8). The input stride technique can compress multiple input characters into a single byte, e.g., compressing four DNA characters to one byte. This technique can increase the input rate, but it may make automata more complicated, thus difficult to route. In the present invention, the input stride is considered as one of the design parameters of the subset encoding method, and the stride technique is combined with the subset encoding for more efficient hardware utilization.

A bounded Hamming distance automaton on the AP was described by Roy and Alum (Document 3) for solving the DNA motif searching problem. For a hamming distance (l, d), that is to match a pattern of length l with at most d substitutions, this traditional design needs $(2d+1)l-2d^2$ STEs. Without the subset encoding, the capacity of each STE is not efficiently utilized. In addition, it is estimated that the capacity assuming the STE utilization efficiency is 80%, but the actual routing results for large l and d might be much worse. In the present invention, new subset-encoded Hamming distance automata, which only use 2d+2 STEs when the pattern is within the STE capacity, is introduced, and it is shown that the new design can achieve a higher pattern density.

The Levenshtein Automaton is an elegant solution for computing edit distance. It is based on dynamic programming and uses ε-transitions. However, when implementing the Levenshtein Automation on the AP, many additional STEs and connections are required for processing *-transitions and ε-transitions, which makes the routing very inefficient. For example, Tracy (Document 7) showed a straightforward implementation of the Levenshtein automata on the AP, but the degree of parallelism was quite limited due to the low routing efficiency. In the present invention, the subset-encoded Levenshtein automata, which allow to separate the large automata into pieces, is introduced to improve the routing.

DOCUMENT LISTS

1. P. Dlugosch, D. Brown, P. Glendenning, M. Leventhal, and H. Noyes, "An efficient and scalable semiconductor architecture for parallel automata processing," *IEEE Transactions on Parallel& Distributed Systems*, no. 12, 2014.
2. V. M. Glushkov, "The abstract theory of automata," *Russian Mathematical Surveys*, vol. 16, no. 5, 1961.
3. I. Roy and S. Aluru, "Finding motifs in biological sequences using the Micron Automata Processor," *IEEE IPDPS*, May 2014.
4. K. Zhou, J. J. Fox, K. Wang, D. E. Brown, and K. Skadron, "Brill tagging on the Micron Automata Processor," *IEEE ICSC*, February 2015.
5. K. Wang, M. Stan, and K. Skadron, "Association rule mining with the Micron Automata Processor," *IEEE IPDPS*, May 2015.
6. C. Bo, K. Wang, J. J. Fox, and K. Skadron, "Entity resolution acceleration using Micron's Automata Processor," *ASBD workshop, with ISCA*, June 2015.
7. T. Tracy II, M. Stan, N. Brunelle, J. Wadden, K. Wang, K. Skadron, and G. Robins, "Non-deterministic finite automata in hardware—the case of the Levenshtein automaton," *ASBD workshop, with ISCA*, June 2015.
8. M. Becchi, *Data structures, algorithms and architectures for efficient regular expression evaluation*. PhD thesis, Dept. of CSE, Washington University, 2009.
9. S. Even, A. L. Selman, and Y. Yacobi, "The complexity of promise problems with applications to public-key cryptography," *Information and Control*, vol. 61, no. 2, 1984.
10. K. Prüfer, U. Stenzel, M. Dannemann, R. E. Green, M. Lachmann, and J. Kelso, "PatMaN: rapid alignment of short sequences to large databases," *Bioinformatics*, vol. 24, no. 13, 2008.
11. B. Langmead, C. Trapnell, M. Pop, and S. L. Salzberg, "Ultrafast and memory-efficient alignment of short DNA sequences to the human genome," *Genome biol*, vol. 10, no. 3, 2009.

SUMMARY

Micron's AP is an innovative reconfigurable hardware accelerator for parallel regular expression matching applications. However, many automata designs on the AP face common problems of limited capacity and inefficient routing. The subset encoding method is a general method for relieving those problems and improving the space efficiency. This method encodes both input strings and patterns into subsets of characters and uses loop structures to match those subsets. Therefore, this method reduces the number of states and connections and leads to some new automata designs including subset-encoded Hamming distance automata and subset-encoded Levenshtein automata. In addition, based on the tradeoff analyzations among strides, input rates, and alphabet sizes given by the subset encoding method, different design decisions can be made for different applications. Experimental results show that by applying the subset encoding method, the space efficiency of automata designs can be improved by a range from 3× to 192×. Furthermore, the subset encoding method will play a greater role on future generation of the AP.

BRIEF DESCRIPTION OF THE DRAWINGS

For a better understanding of the aforementioned embodiments of the invention as well as additional embodiments thereof, reference should be made to the Description of Illustrative Embodiments below, in conjunction with the following drawings in which like reference numerals refer to corresponding parts throughout the figures.

sunset encoding for DNA characters in accordance with some embodiments. The DNA sequence "ATGC . . . " is encoded into a byte sequence "\0\5\10\15 . . . " and a set of characters {0, 5, 10, 15, . . . }. Matching is done by putting the set of characters in a self-loop STE and streaming the set of characters.

Figure 6:
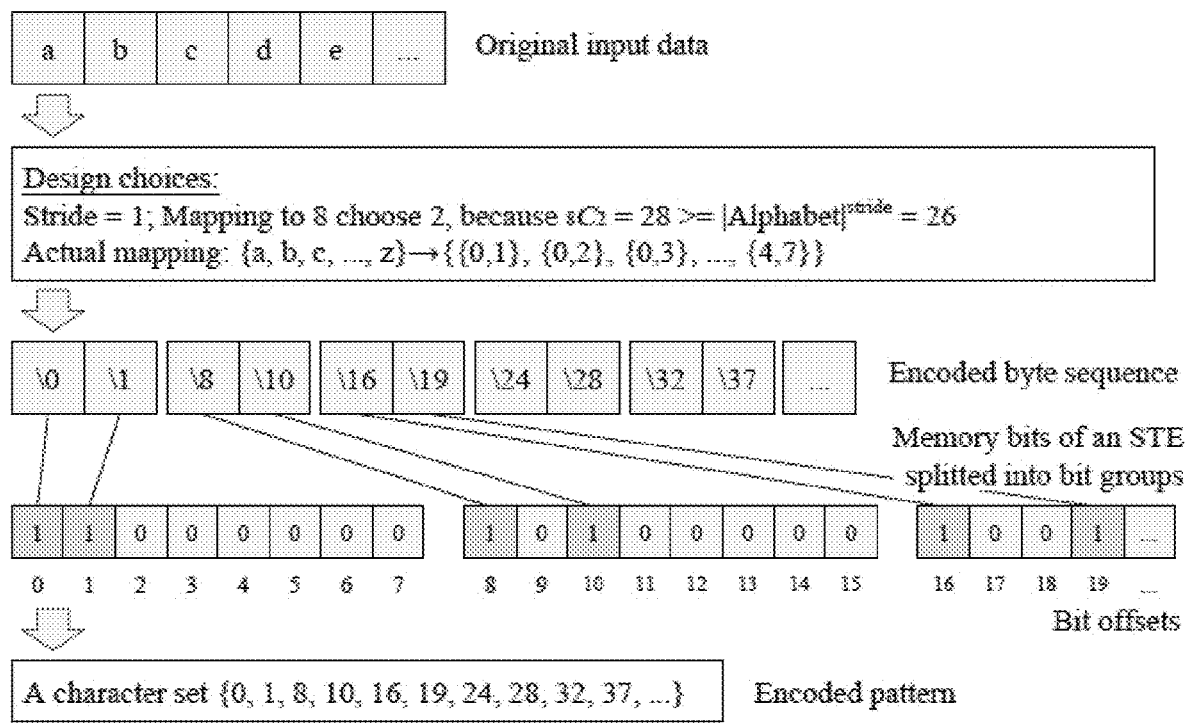

FIG. 6 illustrates the $$\binom{8}{2}$$

sunset encoding for English lowercase letters in accordance with some embodiments. The string "abcde . . . " is encoded into a byte sequence "\0\1\8\10 . . . " and a set of characters {0, 1, 8, 10, . . . }.

Figure 7:
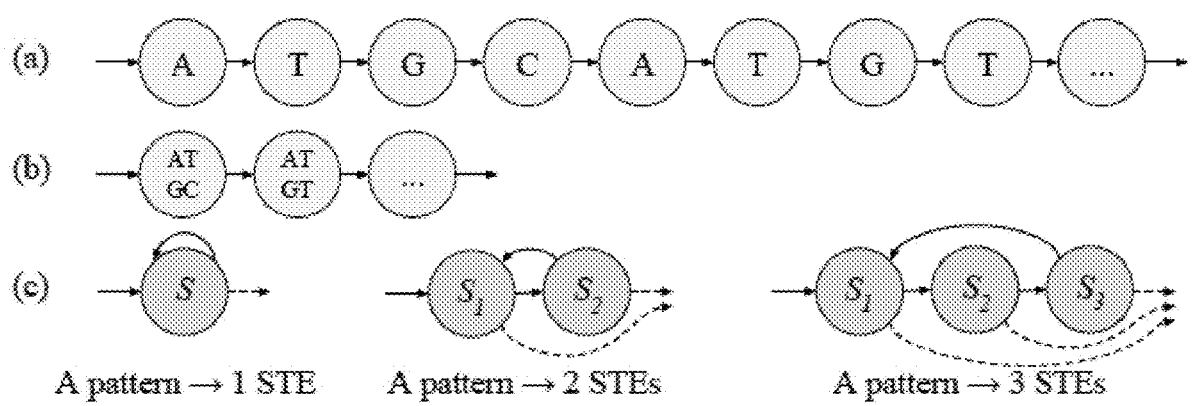

FIG. 7 illustrates exact DNA string matching on the AP in accordance with some embodiments: (a) traditional implementation: n STEs for n DNA characters with 1× input rate; (b) 4-stride implementation: n/4 STEs for n DNA characters with 4× input rate; and (c) subset-encoded implementation: n/64 STEs for n DNA characters with 1× input rate, where $S_i$ is an subset-encoded pattern. The choice of dashed output transition depends on the length of pattern modulo STE count.

Figure 8:
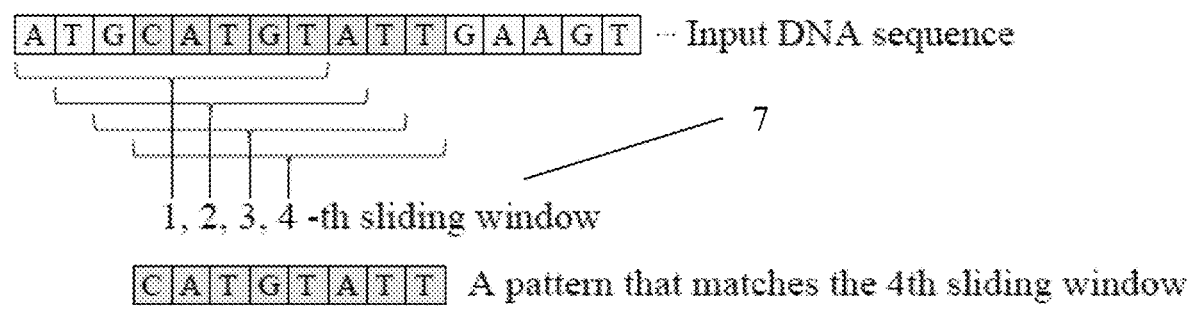

FIG. 8 illustrates sliding windows in matching applications in accordance with some embodiments. Matches can occur on any sliding window.

Figure 9:
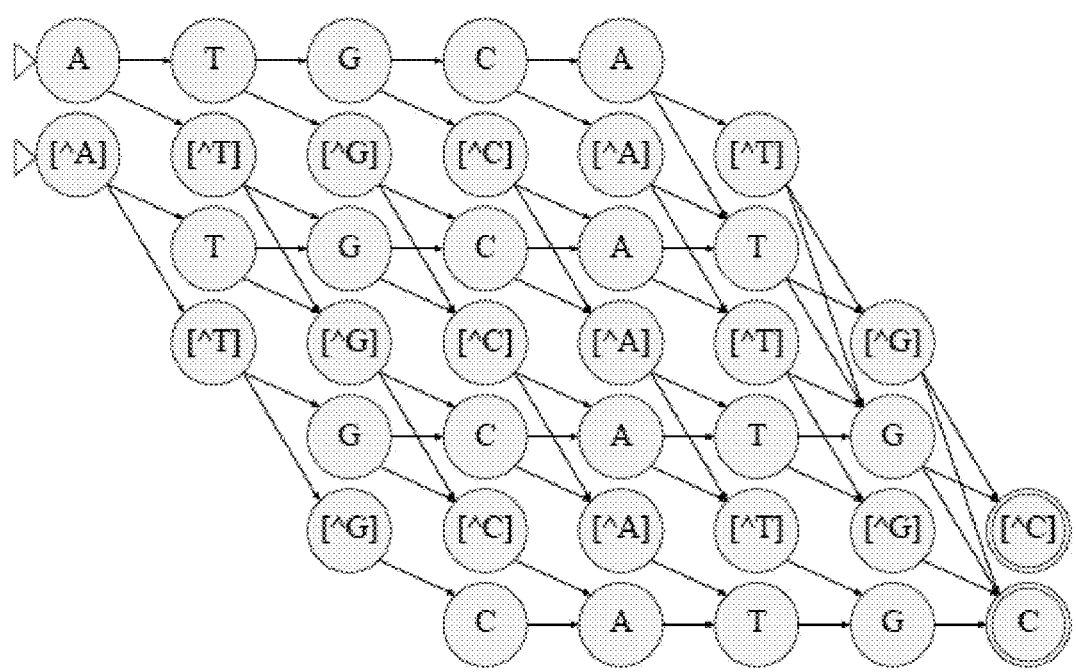

FIG. 9 illustrates traditional Hamming distance automaton (8, 3) for matching the 8-character pattern "ATGCATGC" with a bounded Hamming distance 3 in accordance with some embodiments.

Figure 10:
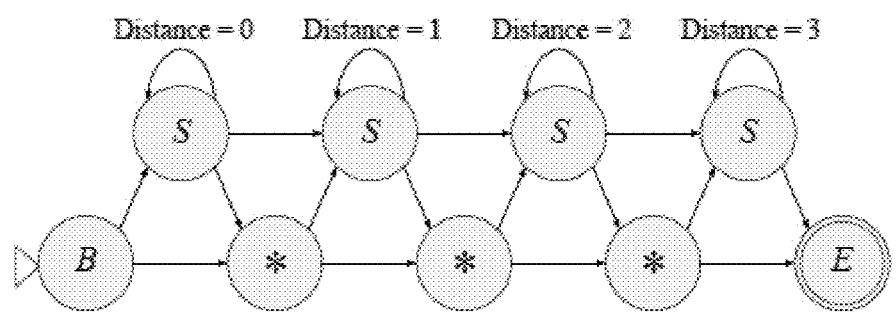

FIG. 10 illustrates subset-encoded Hamming distance automaton (8, 3) for matching an in-put string with a pattern of length 8 within a bounded Hamming distance 3 in accordance with some embodiments. Each mismatch will make the leftmost activated state move one step right. S is the subset-encoded pattern, B is a bit group for controlled beginning, and E is another bit group for controlled reporting. For example, a pattern "ATGCATGC" will be encoded as S={0, 5, 10, 15, 16, 21, 26, 31}, and B can be the eighth bit group {28, 29, 30, 31}, and E can be the first bit group {0, 1, 2, 3}. The "*" is the "any character" wild card symbol used by the AP.

Figure 11:
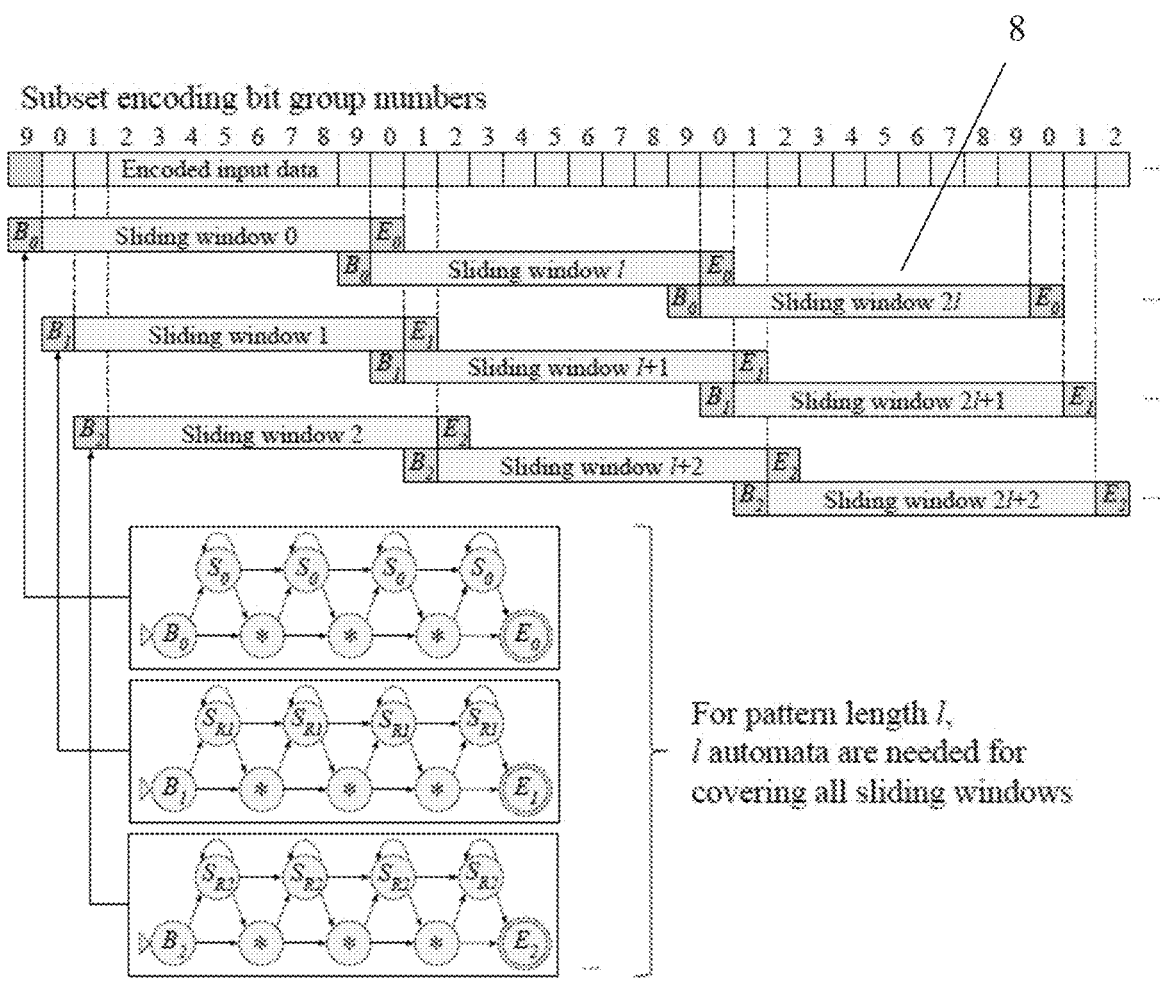

FIG. 11 illustrates a subset-encoded Hamming distance automaton modified to support a sliding window in accordance with some embodiments. This is achieved by replicating a subset-encoded Hamming distance automaton with shifted encodings of the same pattern. In FIG. 11, $S_{Ri}$ represents encoded shifted patterns, and $B_i$ and $E_i$ represent characters from specific bit groups for controlled starting and reporting.

Figure 12:
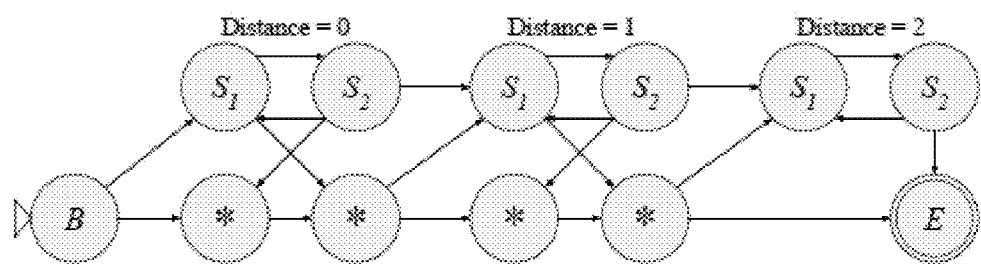

FIG. 12 illustrates subset-encoded Hamming distance automata with 1-to-many encoding in accordance with some embodiments. Two consecutive mismatches may only increase distance by 1.

Figure 13:
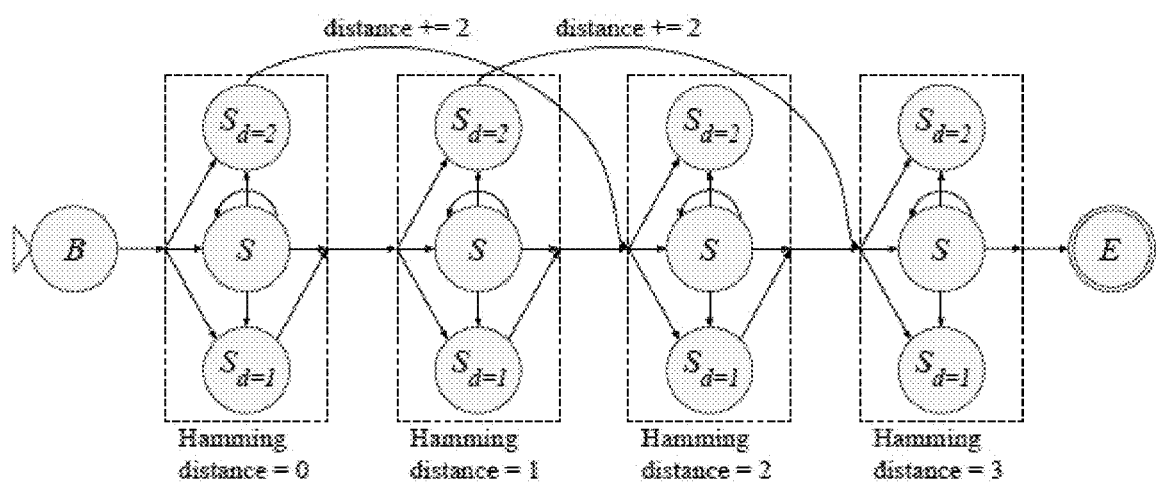

FIG. 13 illustrates 2-stride subset-encoded Hamming distance automaton in accordance with some embodiments. In FIG. 13, S is the encoded pattern, and $S_{d=i}$ contains all neighbors with distance i. The 2-stride mapping function can be F={{AA, AC, AG, AT, CA, . . . , TT}↦{0, 1, 2, 3, 4, . . . , 15}+offset}. For a 2-stride character "AA", S={AA}, $S_{d=1}$={AC, AG, AT, CA, GA, TA}, and $S_{d=2}$={CC, CG, CT, GC, GG, GT, TC, TG, TT}.

Figure 14:
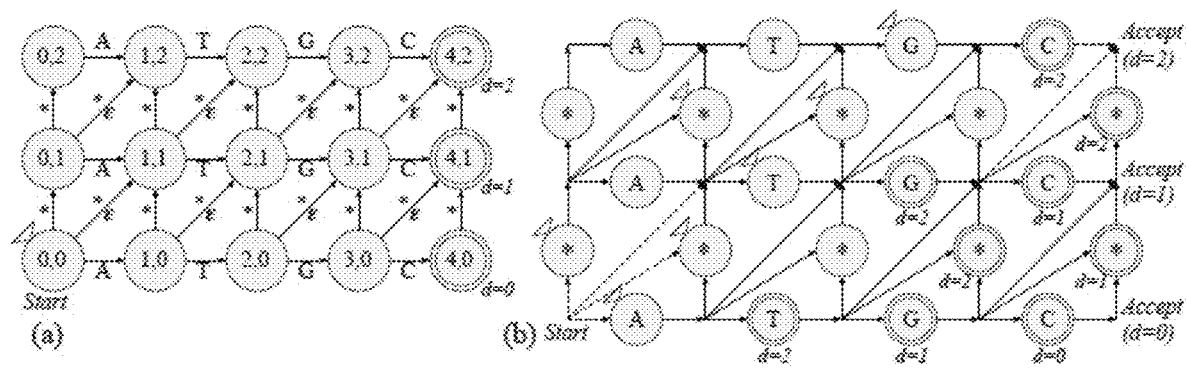

FIG. 14 illustrates classic Levenshtein automata for pattern "ATGC" within edit distance 2 in accordance with some embodiments: (a) traditional NFA representation; and (b) homogeneous Levenshtein Automata on the AP. Insertions are captured by vertical *-transitions. Substitutions are captured by diagonal *-transitions. Deletions are captured by diagonal ε-transitions. Tuples in states are (character offset, edit distance). Many transitions are merged together for simplifying the figure (though they can not be merged on the AP). It is noted that the starting and accepting states are propagated because of the ε-transitions. This structure is routing-intensive due to the large number of transitions.

Figure 15:
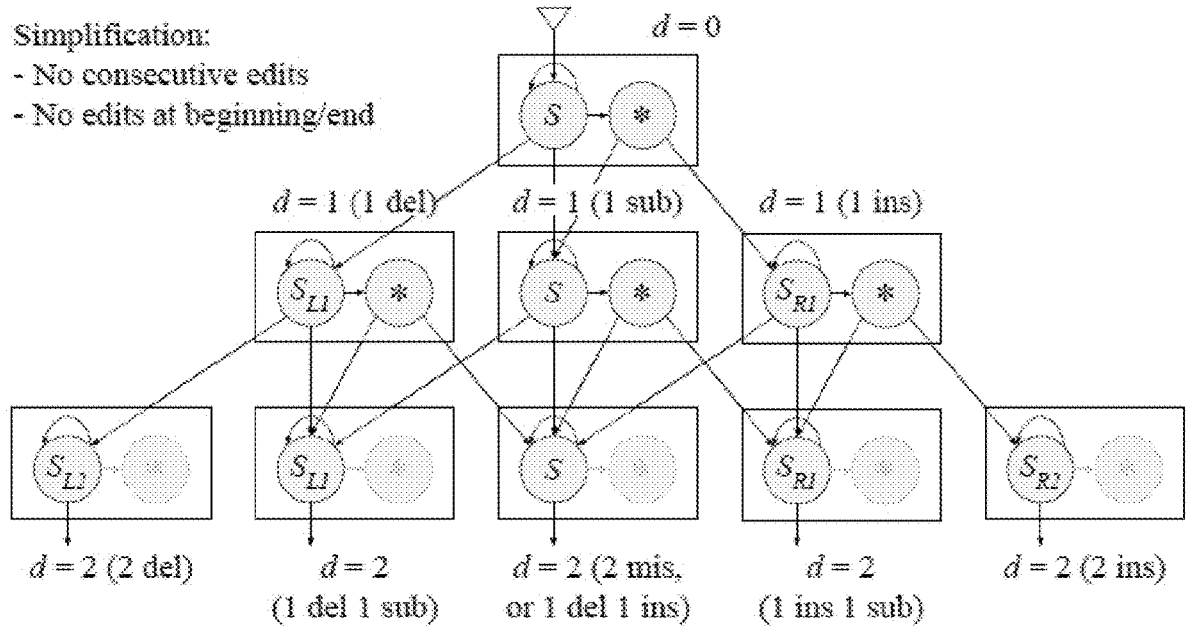

FIG. 15 illustrates a subset-encoded Levenshtein automaton for edit distance ≤2. S, $S_{Li}$, and $S_{Ri}$ are subset-encoded patterns, where $S_{Li}$ and $S_{Ri}$ represent automata shifted i characters left and right, respectively in accordance with some embodiments. A deletion can be captured by jumping from S to its left-shifted pattern $S_L$, while an insertion can be captured by jumping from S to its right-shifted pattern $S_R$ after a substitution. In FIG. 15, d represents edit distance, ins represents an insertion, del represents a deletion, and sub represents a substitution.

Figure 16:
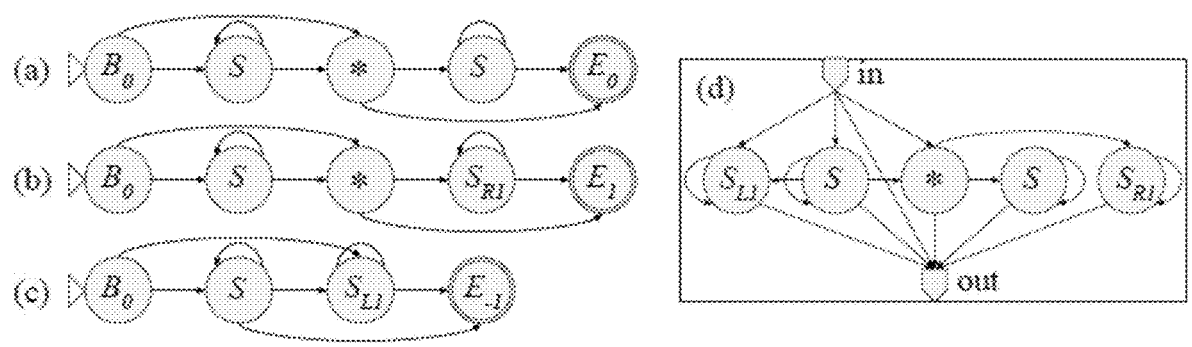

FIG. 16 illustrates separated subset-encoded automata for each type of edit in accordance with some embodiments: (a) 1 substitution; (b) 1 insertion; (c) 1 deletion; and (d) a combined subset-encoded automaton for any 1 edit. A subset-encoded automaton is created for higher edit distance by connecting the output of this widget to three next-level widgets: one each for shift left, shift right, and no shift.

Figure 17:
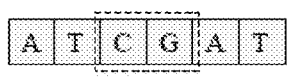
Figure 17:
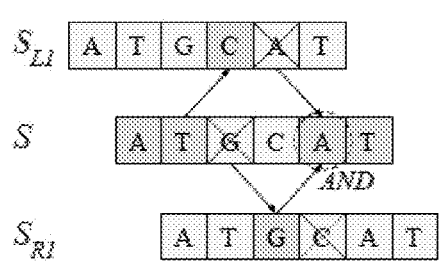
Figure 17:
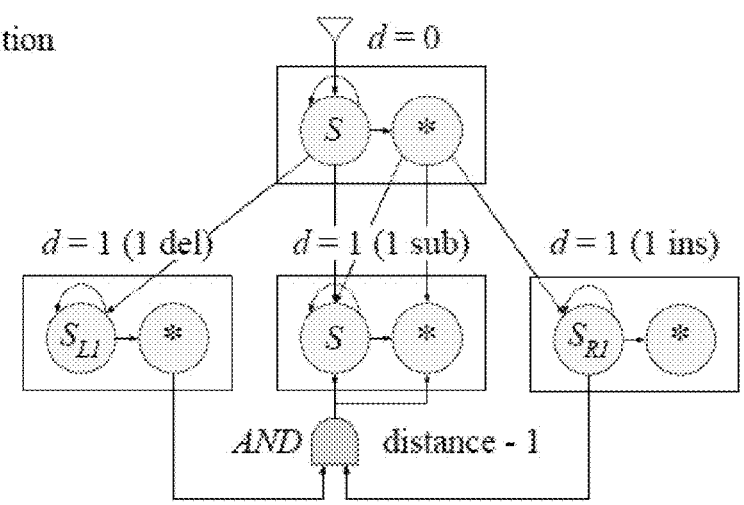

FIG. 17 illustrates a basic structure of the subset-encoded Damerau-Levenshtein automata in accordance with some embodiments. A transposition of adjacent characters should only increase distance by 1. AND gates are used for properly capturing transpositions.

Figure 18:
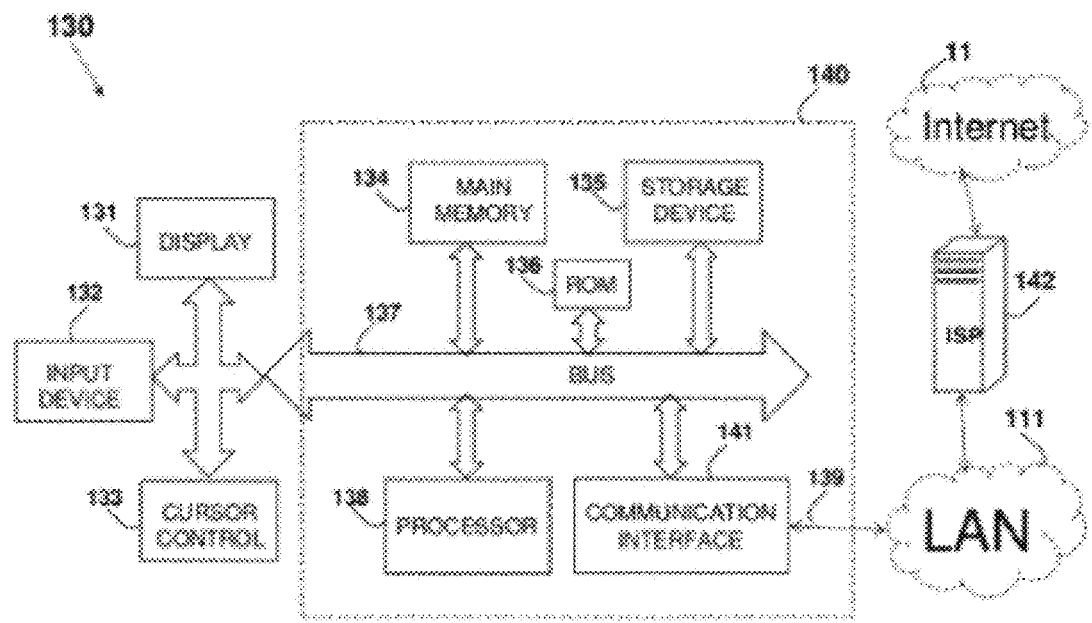

FIG. 18 is a block diagram that illustrates a system including a computer system and the associated Internet connection upon which, an embodiment, or a portion thereof, may be implemented in accordance with some embodiments.

Figure 19:
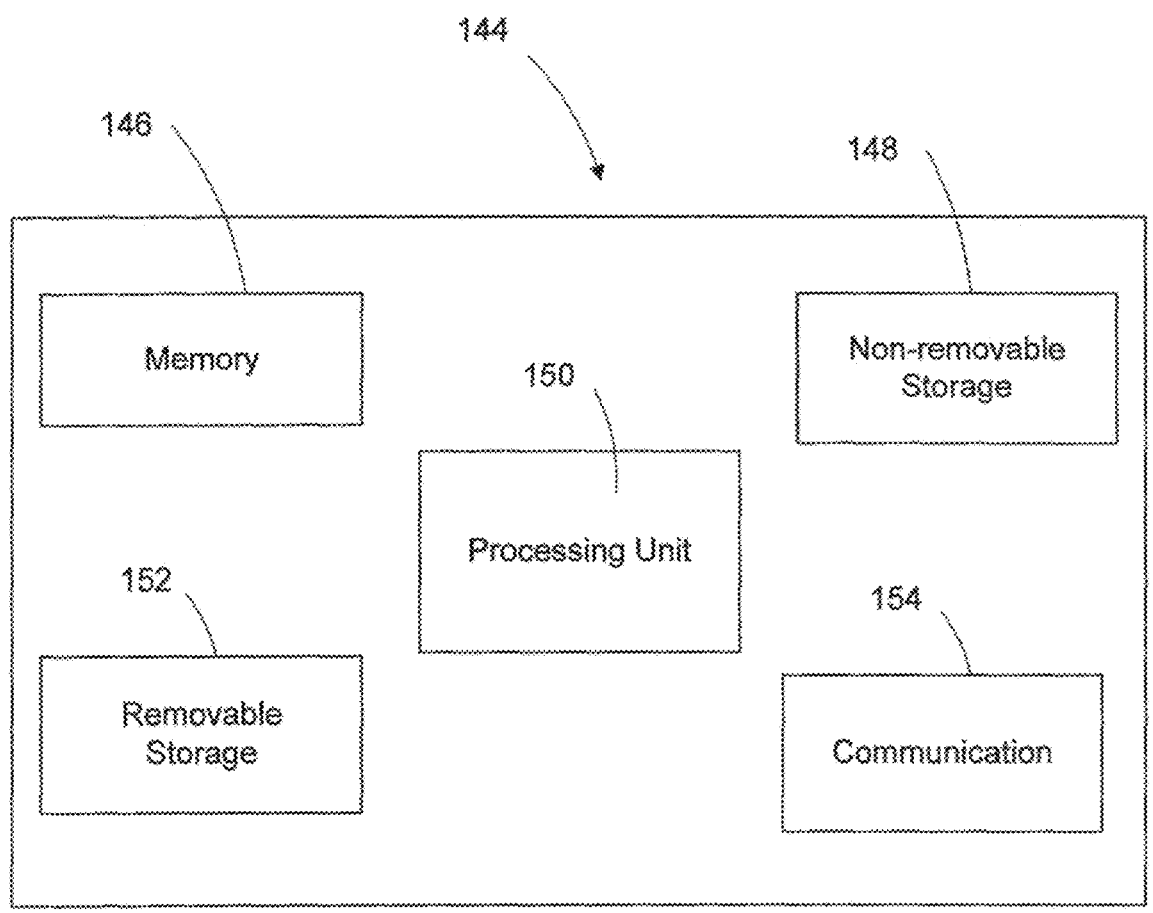
Figure 20:
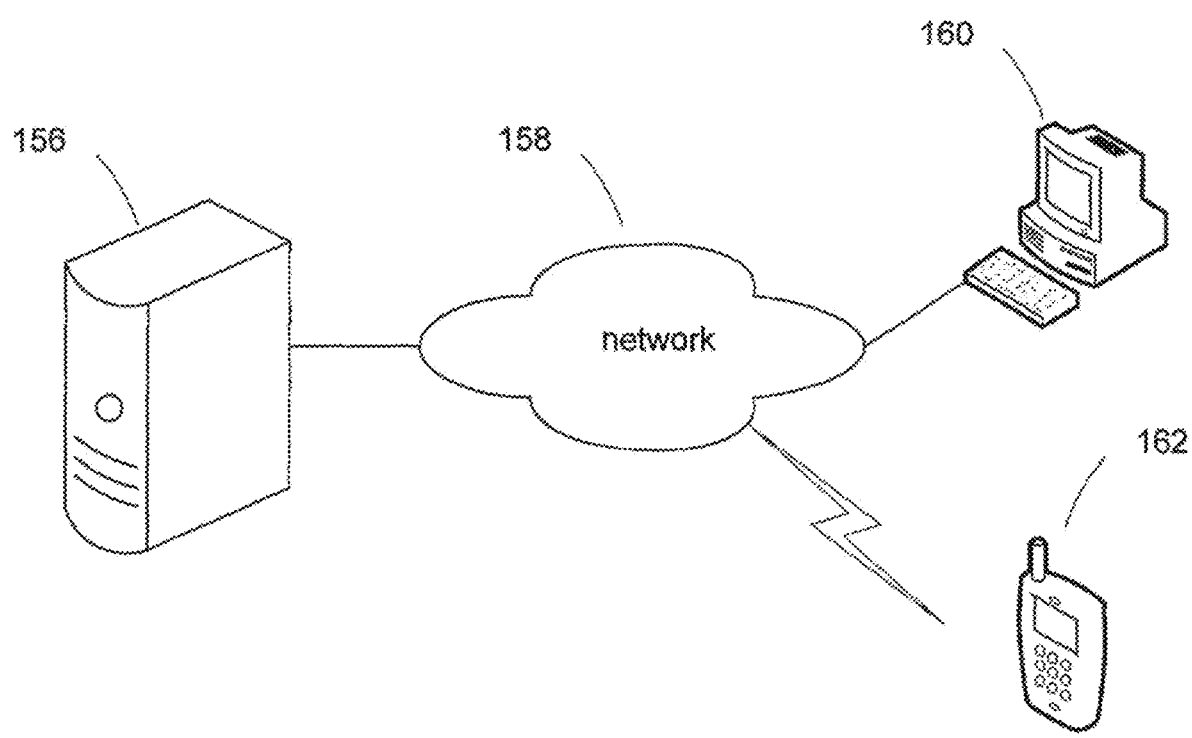

FIGS. 19 and 20 illustrate an exemplary computing device, in which an embodiment of the invention, or a portion thereof, can be implemented.

DESCRIPTION OF ILLUSTRATIVE EMBODIMENTS

Reference will now be made in detail to embodiments, examples of which are illustrated in the accompanying drawings. In the following detailed description, numerous specific details are set forth in order to provide a thorough understanding of the present invention. However, it will be apparent to one of ordinary skill in the art that the present invention may be practiced without these specific details. In other instances, well-known methods, procedures, components, circuits, and networks have not been described in detail so as not to unnecessarily obscure aspects of the embodiments.

Subset Encoding Method

Details of the subset encoding method based on the AP is introduced. The AP architecture, trade-offs between encoding and matching, the problem reduction, and a model for analyzing tradeoffs among design parameters such as stride, alphabet size, and the way of encoding are discussed. The overhead of encoding is also discussed.

The Matching Mechanism of the AP

Figure 3:
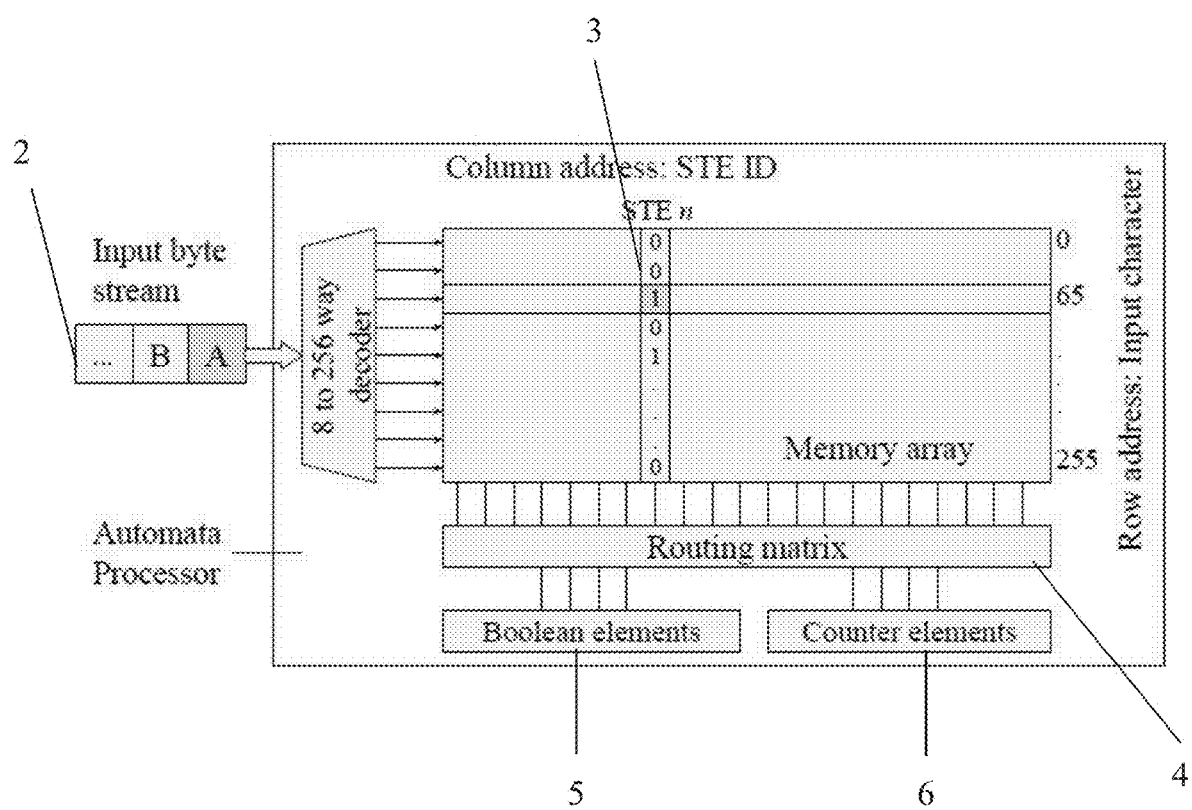
FIG. 3 illustrates the architecture of one AP block. Each row corresponds to one 8-bit input character, and each column corresponds to one STE in accordance with some embodiments. If a memory cell is set to 1, then the input character for its row matches with the STE for its column.

FIG. 3 shows the memory-based architecture of the AP. Each 8-bit input character 2 is decoded as a memory row address. Each 256-bit column 3 in memory represents the matching characteristics of an STE. If a memory cell is set to 1, then the input character for that cell's row matches with the STE for its column. STEs are connected by a routing matrix 4, and some Boolean logic gates 5 and counters 6 are added for extending matching efficiency. Since the matching behavior and routing are represented separately, the user can update the character matching table without reconfiguring the connections. This feature is utilized to gain a performance benefit when the AP has insufficient hardware capacity for all patterns to match against. In this case, computation is performed by making multiple passes on the input data, each time reusing the same automata structures but with different matching characters.

The current AP generation is defined by the following hardware hierarchy:

Each board has 32 chips assembled into 4 ranks with 8 chips each.

Each chip has 2 cores. Automata transitions are not able to span between cores, making the core the limitation on automaton size.

Each core has 96 blocks. These blocks are connected by an inter-block routing matrix, supporting automata transitions among different blocks.

Each block has 256 STEs (32 of which can report off board), 12 reconfigurable Boolean elements, and 4 threshold counters. These are all connected by an intra-block routing matrix, supporting automata transitions between components within that block.

In summary, each AP board can match an input byte stream in parallel over 1.5 million STEs at an input rate of 133 MB/s.

Each AP board is also equipped with an on-board FPGA. Micron has not yet indicated support for users to place functions on the FPGA, but ideally, this acts as an accelerator for potential preprocessing/postprocessing of AP input/output and provides a way to dynamically interact with the AP without CPU intervention.

Redefining Regular Expression Matching Toward Better AP Design

The regular expression matching problem, the general problem which the AP aims to accelerate, seeks to determine whether or not a given input string belongs to the set of strings as defined by a given regular expression. A proper solution to this problem requires answering correctly for every possible input string. In other words, the regular expression matching problem is a decision problem.

It is observed that the encoding function needs not be onto. In other words, not every string is necessarily a valid encoding of some possible input strings. For such strings, the acceptance behavior of the automaton is undefined. In order to solve this new "promise" problem (where the input is promised to be a valid encoding of some strings), the automaton only needs to behave correctly on valid input strings and may behave arbitrarily on all other inputs (Document 9).

The freedom to behave arbitrarily on some input strings results in a greater freedom in automation design. This is responsible for the improved automaton efficiency provided by the subset encoding. The freedom in matching behavior allows for design flexibility in other parameters, such as automaton size, automaton connectivity, or input rate.

Figure 4:
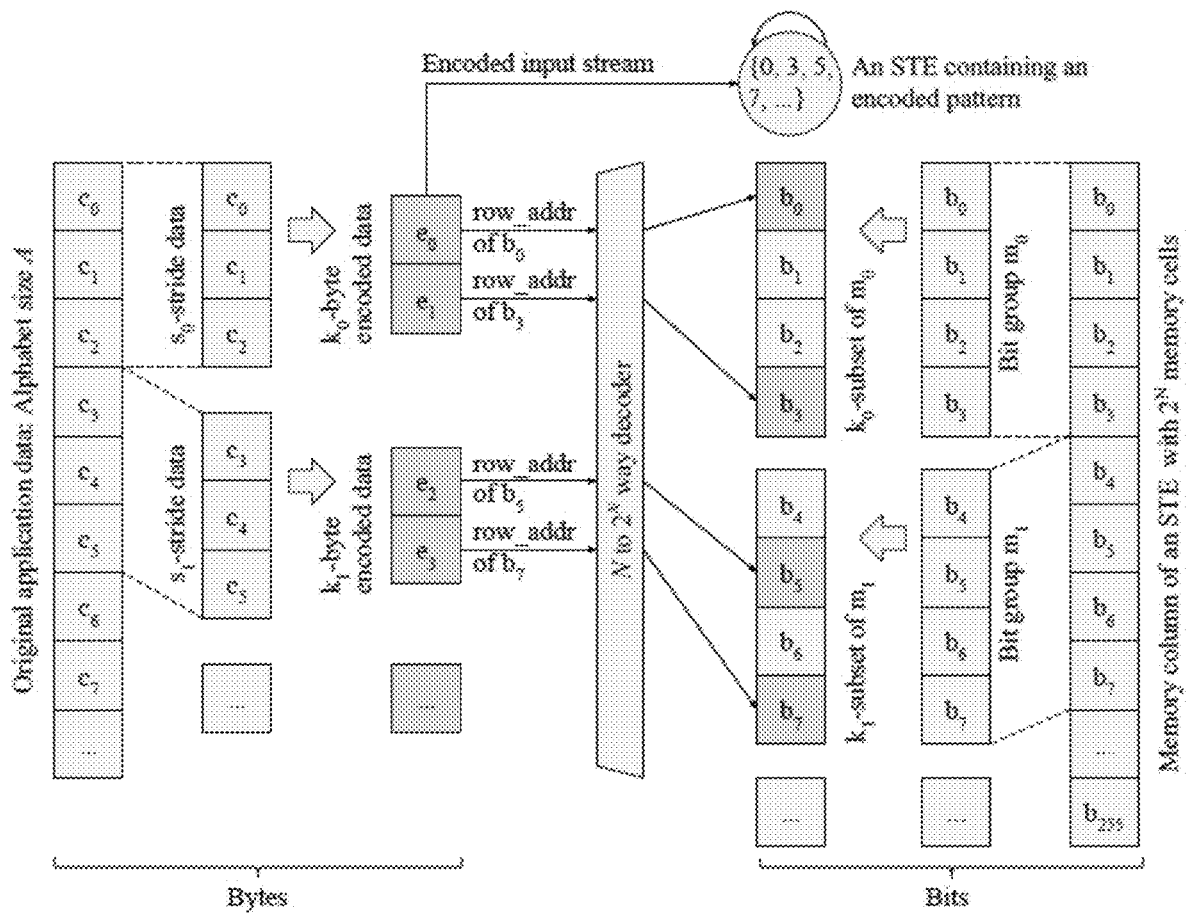
FIG. 4 illustrates the model of the subset encoding method in accordance with some embodiments.

Reducing Matching Decision Problem to Matching Promise Problem by Encoding Input Strings The core idea of the subset encoding method is to convert subsequences of the input sequence into subsets of characters. This then allows a single STE, whose only operation is to match on a subset of characters, to match subsequences of characters. There are many ways one can do this encoding depending on certain design parameters. FIG. 4 shows how to encode a string into subsets of characters considering tradeoffs among design parameters such as stride, input rate and alphabet size. A taxonomy of design parameters are listed as follows:

1) Characteristics of the Input Stream
A: The size of the application data's alphabet ($\Sigma$).
2) Characteristics of the AP Hardware
N: The number of bits in each AP character.
$2^N$: The number of memory cells in one STE.
3) Encoding Design Choices
M, $m_i$: Partition the $2^N$ memory cells into M bit groups, where each group $M_i$ has $m_i$ bits.
$k_i$: Choose $k_i$ bits from group $M_i$, which has $$\binom{m_i}{k_i}$$

different encoding.

$s_i$: Map $s_i$-stride characters (consider $s_i$ consecutive characters as atomic) to group $M_i$.

F: A mapping from $s_i$-stride application data to $k_i$-subset of groups $M_i$, represented as a positive integer. For a sequence of characters the offsets of related bit groups should be added with the final encoding:

$$F = \left( \sum^{s_i} \mapsto \binom{\{0, \ldots, m_i - 1\}}{k_i} \right) + \textit{offset}_i, \quad (1)$$

where the offset of the i-th bit group is:

$$\textit{offset}_i = \sum_{j=0}^{(i \bmod M)-1} m_j. \quad (2)$$

In summary, offset information is encoded together with the input data so that a specific character will only match with its corresponding bit group. The offset will roll back to zero when it exceeds the length of the longest pattern.

All of the above encoding design choices may be made independently under the following constraints:

4) Constraints

The total number of bits in all bit groups are bounded by the number of memory cells in each STE:

$$\sum_{i=0}^{M-1} m_i \leq 2^N. \quad (3)$$

When picking $k_i$ bits out of $m_i$ bits, maximum value of $\binom{m_i}{k_i}$ occurs when $k_i = m_i/2$. So, it must hold that:

$$1 \leq k_i \leq m_i/2. \quad (4)$$

When mapping from $s_i$-stride characters to $k_i$-subset of $m_i$ bits, we need to ensure that the number of subsets exceeds the number of all possible $s_i$-stride characters:

$$A^{s_i} \leq \binom{m_i}{k_i}. \quad (5)$$

5) Encoding Results

The capacity of a single STE, i.e., how many original input characters can be encoded in one STE:

$$\text{Capacity}_{STE} = \sum_{i=0}^{M-1} s_i. \quad (6)$$

The actual input rate after encoding, i.e., how many original input characters can be processed per second:

$$\text{InputRate}_{Encoded} = \frac{\sum_{i=0}^{M-1} s_i}{\sum_{i=0}^{M-1} k_i} \times \text{InputRate}_{AP}. \quad (7)$$

In practice, constant numbers are picked for stride $s_i$, subset size $k_i$ and bit group size $m_i$. As a result, the subset encoding method can be applied, and the encoding performance is analyzed with the following steps:
1. Determine the characteristics of the input data and the AP hardware, such as the input alphabet size A and the number of bits $2^N$ in each STE.
2. Choose design parameters, including stride s, bit group size m, and subset size k, such that $$A^s \le \binom{m}{k}.$$

3. Design a constant-time encoding function to map each s-stride input character to a k-subset out of m bits, and add bit group offsets to the final encoding.
4. Calculate capacity and input rate. After encoding, an STE can contain $s \times 2^N/m$ original input characters, and the actual input rate will be s/k times the input rate of the AP.

Subset Encoding Examples

Two examples of encoding following the above procedure are shown. One example encodes DNA characters with 4 memory cells each, and the other example encodes English lowercase letters with 8 memory cells each. As a result, an 8-bit STE can contain 64 DNA characters or 32 English letters.

DNA Characters

1. The alphabet size of DNA is A=4. Assuming a pattern of length 64, a single-stride DNA character is mapped to $$\binom{4}{1}$$

Figure 1:
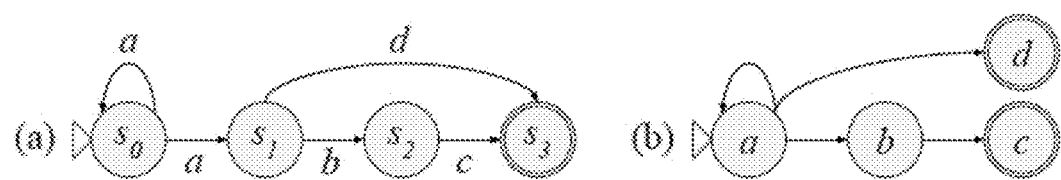
FIG. 1 illustrates two equivalent NFA representations for pattern a+(bc|d): (a) traditional NFA; (b) homogeneous NFA (the model of the AP) in accordance with some embodiments.
Figure 2:
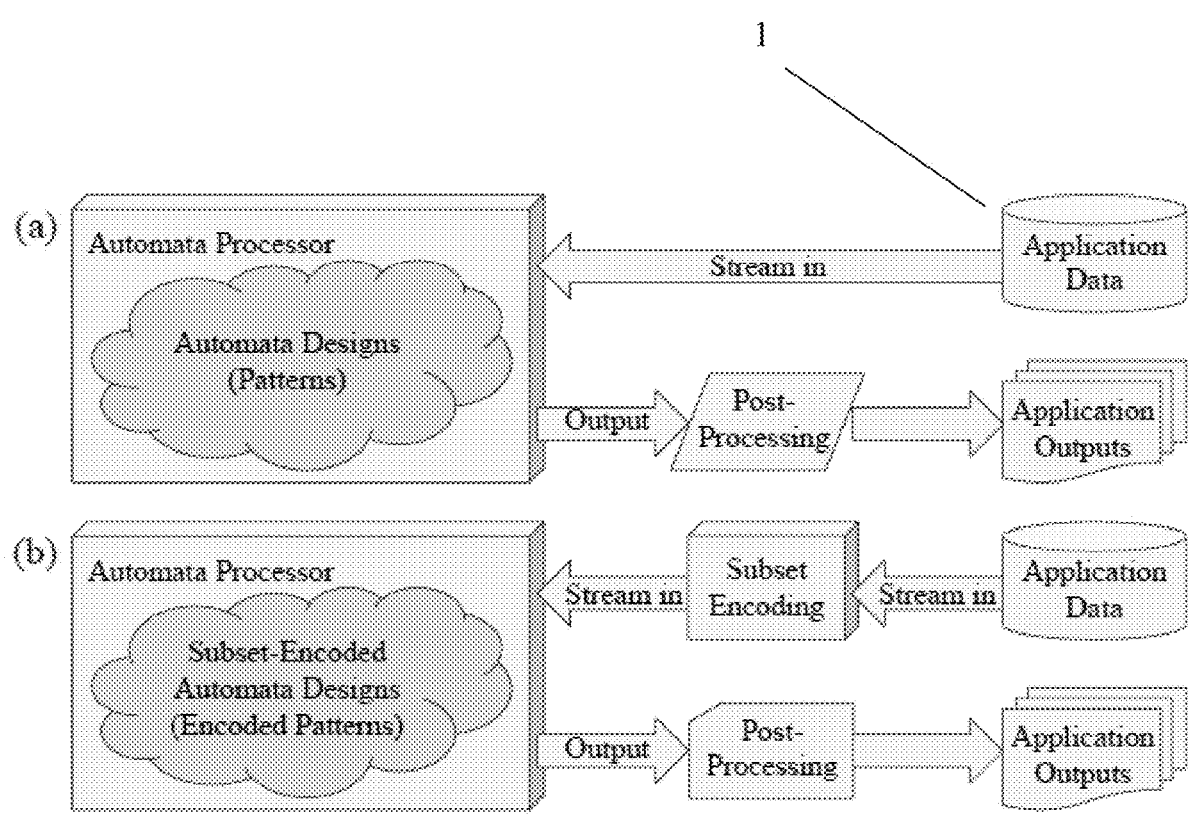
FIG. 2 illustrates overview of the subset encoding method: (a) the typical AP execution flow; (b) the execution flow after the subset encoding method in accordance with some embodiments.
Figure 5:
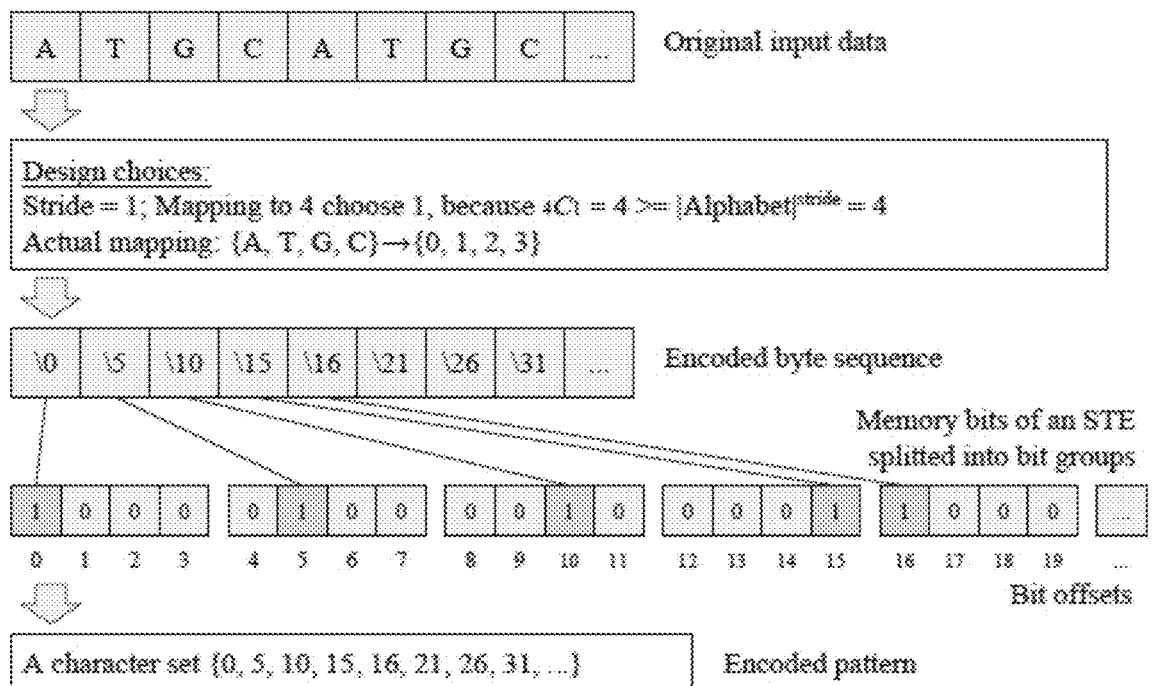
FIG. 5 illustrates the $$\binom{4}{1}$$

(1 bit is enabled for every group of 4 bits in the STE memory column), as shown in FIG. 5
2. Design choices under the constraint $$A^s \le \binom{m}{k};$$

Stride s=1, bit group size m=4, subset size k=1. A single STE can contain $2^N/m=64$ bit groups, and the pattern has M=64 bit groups.
3. The encoding function F can be a one-on-one mapping: F={{A, T, G, C} ↦ {0, 1, 2, 3}}+offset, where for the n-th DNA character, offset=(n mod M)×4=(n mod 64)×4.
4. As a result, the capacity of a single STE is $2^8/4=64$, and the input rate after encoding is s/k=1/1=1×, the same as the input rate of the AP.

English Lowercase Letters

1. The alphabet size of English lowercase letters is A=26, so assuming a pattern of length 32, a single-stride English letter is mapped to $$\binom{8}{2}$$

where $$A^1 = 26 \le \binom{8}{2} = 28,$$

as shown in FIG. 6.
2. Design choices under the constraint $$A^s \le \binom{m}{k};$$

Stride s=1, bit group size m=8, subset size k=2. A single STE can contain $2^N/m=32$ bit groups, and the pattern has M=32 bit groups.

TABLE 1

Subset Encoding Tradeoff Examples – DNA $\left( {}_mC_k = \binom{m}{k} \right)$

| Stride | Encoding | STE Capacity | Input Rate | Efficiency Factor |
|---|---|---|---|---|
| 1 | $_{256}C_1$ | 1 | 1.0x | 1.0 |
| 1 | $_4C_1$ | 64 | 1.0x | 64.0 |
| 2 | $_{16}C_1$ | 32 | 2.0x | 64.0 |
| 2 | $_7C_2$ | 72 | 1.0x | 72.0 |
| 2 | $_6C_3$ | 84 | 0.67x | 56.0 |
| 4 | $_{256}C_1$ | 4 | 4.0x | 16.0 |
| 4 | $_{24}C_2$ | 40 | 2.0x | 80.0 |
| 4 | $_{13}C_3$ | 76 | 1.33x | 101.3 |
| 4 | $_{11}C_4$ | 92 | 1.0x | 92.0 |
| 125 | $_{256}C_{127}$ | 125 | 0.98x | 123.0 |

3. The encoding function F maps each character to a 2-subset out of 8: F={{a, b, c, . . . , z} ↦ {{0, 1}, {0, 2}, {0, 3}, . . . , {4, 7}}+offset, where for the n-th character in the input stream, offset=(n mod M)×8=(n mod 32)×8.
4. As a result, the capacity of a single STE is $2^8/8=32$, and the input rate after encoding is s/k=1/2=0.5×. 32 English lowercase letters are encoded in one self-loop STE in exchange for halving the input rate.

Subset Encoding Tradeoff Analysis

There are many tradeoffs among the alphabet size of application data, input stride, input rate, and subset encoding complexity. These tradeoffs are analyzed based on the model of the subset encoding method.

From equation (5), given the alphabet size A of the application data, the stride s is bounded by bit group size m and subset size k. A larger stride s means faster input rate, but larger k and m are needed to be chosen to satisfy the constraint. However, when m is increased, fewer bit groups need to be put in an STE. When k is increased, the input rate decreases, and the complexity of encoding is increased.

Table 1 shows how strides and encoding approaches affect the STE capacity and the input rate. Given a stride, there are many different encoding approaches to use. The efficiency factor, which is the product of STE capacity and the input rate, roughly indicates encoding efficiency. Subset-encoded automata achieve better efficiency than traditional multiple-input stride implementations (Document 8), since traditional designs only map 4-stride DNA characters to $\binom{256}{1}$.

Encoding Overhead Analysis

Since some computational burden is moved from the matching phase to the encoding phase, there is an encoding overhead. To encode each character, a one-to-one character-to-subset mapping needs to be done, and the bit group offset needs to be added to the encoding. For a small subset size k, the mapping can be done through simple arithmetic calculation or table lookup. However, if k is large, it may be difficult to efficiently map input data to subsets, and the encoding rate may be slower than the input rate of the AP.

As long as the rate of data encoding is greater than the input rate of the current AP hardware (133 MB/s), then the encoding step is effectively "free" when pipelined with the input stream on either a CPU or FPGA. The experiments show that the subset encoding of DNA sequences can be easily computed at a rate of more than 140 MB/s with a C program on a 2.7 GHz single-threaded CPU. The subset encoding on CPU can be pipelined with the AP by splitting the input sequence into chunks and sending encoded chunks to the AP through PCIe interface. In the case that the same input will be used many time with the same encoding, the encoded DNA sequences can be stored so that encoding them multiple times is not necessary.

Subset-Encoded Automata Designs

Some automata designs applying the subset encoding method are introduced, including exact matching automata, Hamming distance automata, Levenshtein automata, and Damerau-Levenshtein automata.

Exact String Matching

The exact string matching problem determines if a given input string is exactly the same as a given pattern. Traditional designs put string patterns in singly linked STE chains and use each STE to match with one character or one stride of characters, as shown in FIGS. 7(*a*) and (*b*).

In many applications, whether a pattern matches with any substring in a long input sequence needs to be determined. In this case, it is important to support a sliding window matching procedure. As shown in FIG. 8, a sliding window 7 is a fixed length window which, as it moves over the input stream, defines a substring to match against the given pattern. The AP simulates NFA transitions in lock-step, which means each input character can only match with successors of currently activated STEs, and there are no ε-transitions. Thus, a singly linked STE chain can match with a longer input sequence in a pipelined way and produce results on every cycle. In other words, the matching results of every sliding window of the length of the pattern along the entire input sequence can be obtained.

However, the character-OR ability of STEs are not efficiently utilized, especially when sliding windows are not required, or when the application alphabet size is very small.

If the subset encoding method is applied, a sequence of data can be compressed into one STE, as shown in FIG. 7(*c*). For longer patterns, multiple STEs can be used to construct a loop structure, then the first character can be put into the first STE, and the second character can be put into the second STE, and etc. On the current generation of the AP, up to 64 DNA characters can be encoded into one STE, so n/64 STEs for n consecutive DNA characters are needed. As a result, for those applications in which sliding windows are not required, 64× more patterns can be placed than straightforward implementations, and 16× more patterns can be placed than 4-stride implementations on the same amount of hardware.

For supporting sliding windows, the subset-encoded automata need to be replicated multiple times. As a result, in some cases the encoded automaton may have more states than the traditional automaton. Even in this case, the encoded automaton may still have a routing advantage.

Subset-Encoded Hamming Distance Automata

Traditional Hamming distance automata designs (Document 3) use $(2d+1)l-2d^2$ STEs for a bounded Hamming distance (l, d). An example of Hamming distance (8, 3) is shown in FIG. 9. This automata structure supports sliding windows over the input stream. However, for large l and d, the resulting automata are difficult to route on the AP, achieving only 16% STE utilization for the (60, 10) case.

A subset-encoded Hamming distance automaton for (l, 3) is shown in FIG. 10. For a Hamming distance d, a d-level ladder structure is constructed to match input strings with patterns within distance d. The STEs in upper row are self-loop STEs containing an encoded pattern so that they remain activated as long input characters match with the patterns. The lower row of STEs capture mismatches. As a result, when a substitution occurs, the leftmost activated self-loop STE will be turned off, and the activation state will move one step right. If the number of substitutions is ≤d, this automaton will accept the input string. Otherwise, the activation chain will exit this structure, thus all STEs will be shut down before reaching the end of the input, and there will be no report at the end.

Compared to the straightforward Hamming distance automata in FIG. 9, which needs $(2d+1)l-2d^2$ STEs, the subset-encoded Hamming distance automata only use 2d+2 STEs for a Hamming distance (l, d) when l≤64. This new subset-encoded automata design can significantly reduce the automata size, improving routability in hardware. For example, for a Hamming distance (64, 10), the traditional solution needs 1144 STEs, while the subset-encoded solution only uses 22 STEs, which is a 52× improvement.

The above subset-encoded Hamming distance structure (which only decides whether the in-put was within distance d of the pattern) can be easily extended for calculating the actual Hamming distance (which finds the number of substitutions required to transform the input into the pattern). To do this, extra reporting STEs are linked to the self-loop STEs in the upper row of FIG. 10 to find the actual number of substitutions. Alternatively, the threshold counters can be used with the subset-encoded automata to count the Hamming distances. The counter solution uses fewer STEs than the former solution. However, since counters are a scarce resource on the AP (there are 768 counters per core), they are best used for a large distance d.

Hamming Distance Automata with Sliding Windows

Many pattern matching applications, such as DNA alignment, require matching a long input sequence with some short patterns and determine the start positions of all matching subsequences. A single subset-encoded Hamming distance automaton cannot naively support this sliding window approach, since STEs are reused for a sequence of input data.

To support sliding windows, the subset-encoded Hamming distance automata are replicated, as shown in FIG. 11. The key ideas for supporting sliding windows include: 1) replicate the subset-encoded Hamming distance automata l times; 2) each replicated automaton contains a unique shift of the given pattern; and 3) using characters from a particular bit group in starting and reporting STEs to control when to start matching and when to report. For example, the result of shifting pattern "$c_0 c_1 c_2 \ldots c_n$" one step right is "$c_n c_0 c_1 \ldots c_{n-1}$". This shifted pattern can match with string "$c_0 c_1 c_2 \ldots c_n$" starting from different positions.

As will be discussed below, up to 192× more subset-encoded Hamming distance automata can be placed on the AP. In the sliding window case, up to 3.2× more patterns can be placed than traditional Hamming distance automata, even if the subset-encoded automata are replicated l times.

One-to-Many Encoded Hamming Distance Automata

A one-to-many encoding (stride s=1, subset size k>1) will decrease the input rate (since the encoded data is longer than the application data), but it can allow to encode even more characters into each STE, because according to Equation 5, a larger k will allow to decrease m. For example, if English lowercase letters are mapped to 1-subsets of 26 bits, only 9 English letters are encoded into one STE. But if English lowercase letters are mapped to 2-subsets of 8 bits, 32 English letters can be encoded into one STE.

Because each input character is encoded to multiple bytes, multiple mismatches related to the same original input character should only increase Hamming distance by 1. For example, letter "a" can be encoded to "0, 1", when "0, 2" (the encoding of letter "b") is inputted, there is one mismatch, while when "1, 2" (the encoding of letter "h") is inputted, there are two mismatches. However, both cases should increase distance by 1. As a result, extra STEs are needed to delay the activations to correctly count the Hamming distance.

FIG. 12 shows the one-to-many subset-encoded automaton for a Hamming distance (32, 1) of English lowercase letter patterns. The ladder structure is similar to FIG. 10, except that the 2-subset encoding of characters are put into two STEs. For example, 'a' will be encoded as a 2-subset {0, 1}. Then, '0' is put in the first STE, and '1' is put in the second STE.

Multiple-Input Stride Hamming Distance Automata

When patterns are too short to fully utilize an STE, multiple-input stride can be used to increase the input rate, and more data can be encoded into each STE. As the dual to one-to-many encoding, a single mismatch with multiple-input stride encoding may represent multiple substitutions between the input sequence and the pattern. For example, if 2-stride DNA characters "AC" are encoded into a single encoding "1", a mismatched input "2" (encoding of "AG") should increase Hamming distance by 1, while another mismatched input "15" (encoding of "TT") should increase Hamming distance by 2. Thus, when a mismatch occurs, the actual Hamming distance needs to be distinguished. The subset encoding method can conveniently support this by separating encoded alphabet into multiple sets according to actual Hamming distances.

FIG. 13 shows an example of encoding 2-stride DNA characters into $$\binom{16}{1}.$$

32 DNA characters can be encoded into one STE, and a 2× input rate increase can be achieved. The 16 combinations of two DNA characters are mapped to numbers from 0 to 15. For each specific combination of two DNA characters, two STEs are used to separate the distance-1 neighbors and distance-2 neighbors. If a distance-1 mismatch occurs, one step is moved to the right on the ladder structure, and if a distance-2 mismatch occurs, two steps are moved to the right.

Subset-Encoded Levenshtein Automata

The Levenshtein distance or edit distance is the minimum number of edits that can convert one string to the other. An edit can be an insertion, a deletion, or a substitution. In practice, the edit distance can be used in DNA alignment or spell correction. A classic dynamic-programming-based Levenshtein automaton is shown in FIG. 14(a). When implementing Levenshtein automata on the AP, extra STEs and more connections to support *-transitions and ε-transitions are needed, and the start and accept states need to be propagated along the ε-transitions, as in FIG. 14(b). As a result, the large automata structures make routing very inefficient, or even impossible (Document 7).

By applying the subset encoding method, smaller Levenshtein automata, which can significantly increase the routing efficiency, can be designed. The subset-encoded Levenshtein automata are adapted from the subset-encoded Hamming distance automata. The key idea is that a deletion can be captured when an activation transfers to a left-shifted pattern, and an insertion can be captured when an activation transfers to a right-shifted pattern after a substitution.

A subset-encoded Levenshtein automaton within distance 2 is shown in FIG. 15. For patterns that fit into one STE, the total number of STEs only depends on the distance. As a result, this new design can achieve higher utilization and pattern density on the AP.

The subset-encoded Levenshtein automata provide two levels of separation: 1) using separated automata to support sliding windows; and 2) using separated automata to recognize different edits. The three separated subset-encoded Levenshtein automata for one substitution, insertion and deletion are shown in FIGS. 16(a), (b) and (c), respectively. These three types of automata are combined together to construct a widget for edit distance 1, as shown in FIG. 16(d). A subset-encoded automaton is created for higher edit distance by connecting the output of this widget to three next-level widgets: one each for shift left, shift right, and no shift.

Subset-Encoded Damerau-Levenshtein Automata

The Damerau-Levenshtein distance is an extended version of edit distance that considers the distance of transposition of adjacent characters as a singular edit. The subset-encoded Levenshtein automaton is modified to support Damerau-Levenshtein distance by adding AND gates. The idea here is that if a single edit can be considered as any of an insertion, deletion, or substitution then that edit could also be considered a transposition. The basic structure of the subset-encoded Damerau-Levenshtein automata is shown in FIG. 17. While traditional Levenshtein automata will count transposition as distance 2, this new structure uses AND gates (supported on the AP using Boolean elements) to increase distances by only 1 for transposition.

Supporting General Regular Expressions

Besides the automata designs shown in previous sections, there are many other ways to design automata with the subset encoding method, which provides a huge potential to improve the space efficiency. For example, the subset encoding method can support general regular expressions with a large alphabet size, such as 4-byte characters, because these characters of large alphabet size can be mapped to subsets, which can be put in one STE. In addition, the wild card character "." (or "*" on the AP) can be represented by setting all bits in a bit group to 1. The OR operation in regular expressions is implemented by setting unions of subsets to 1, though ambiguities arise from one-to-many encoding.

Experimental Results

To evaluate the efficiency and performance of the proposed subset encoding method, both compiling results and running time of DNA k-mer searching using real-world data are shown. The compiling results of automata are collected from the Micron AP SDK compiler. The AP execution time is derived using the 133 MB/s input rate and the compiling results. Single-threaded CPU experiments are run on servers with 3.3 GHz Intel® i7-5820K CPU and 32 GB RAM.

Compiling Results for Hamming Distance Automata

To demonstrate the benefit of the subset encoding method, the compiling efficiency between the traditional Hamming distance automaton and the subset-encoded Hamming distance automaton

TABLE 2

Compiling Results of Hamming Distance Automata

| D | $SE_d$ | $C_{30,d}$ | $X_{30,d}$ | $X_{1/30}$ | $C_{60,d}$ | $X_{60,d}$ | $X_{1/60}$ |
|---|---|---|---|---|---|---|---|
| 1 | 3072 | 120 | 25.6x | 0.9x | 60 | 51.2x | 0.9x |
| 2 | 1536 | 50 | 30.7x | 1.0x | 16 | 96.0x | 1.6x |
| 3 | 1536 | 24 | 64.0x | 2.1x | 12 | 128.0x | 2.1x |
| 4 | 960 | 24 | 40.0x | 1.3x | 8 | 120.0x | 2.0x |
| 5 | 960 | 16 | 60.0x | 2.0x | 6 | 160.0x | 2.7x |
| 6 | 768 | 12 | 64.0x | 2.1x | 6 | 128.0x | 2.1x |
| 7 | 768 | 10 | 76.8x | 2.6x | 4 | 192.0x | 3.2x |
| 8 | 576 | 9 | 64.0x | 2.1x | 4 | 144.0x | 2.4x |
| 9 | 480 | 9 | 53.3x | 1.8x | 4 | 120.0x | 2.0x |
| 10 | 480 | 6 | 80.0x | 2.7x | 3 | 160.0x | 2.7x |

D: Hamming distance
$SE_d$: # of subset-encoded Hamming-dist automata per core
$C_{30,d}$, $C_{60,d}$: # of traditional Hamming-dist automata (30, d) and (60, d) per core
$X_{30,d}$, $X_{60,d}$: Speedup of the subset encoding method on (30, d) and (60, d)
$X_{1/30}$, $X_{1/60}$: Speedup of the subset encoding method when replicate l times to support sliding window on (30, d) and (60, d) are first compared (Table 2). Traditional implementations use the structure shown in FIG. 9. The subset-encoded Hamming distance automata use the more succinct ladder structure shown in FIG. 10.

For a Hamming distance (l, d), the subset-encoded automata need to be replicated to support the sliding windows 8, as shown in FIG. 11. Compiling results show that even if the subset-encoded automaton is replicated l times (thus divide the number of patterns by l), up to 3.2× more patterns can be placed on the AP. If the sliding window is not required, scaling is unnecessary, thus subset encoding can place up to 192× more patterns than traditional solutions.

DNA k-Mer Searching

The problem of matching DNA/RNA k-mers against reference sequences to identify regions of similarity is ubiquitous, as it is essential to many biological applications. The contribution of the

TABLE 3

DNA Hamming Distance on 200 MB input and 20,000 25-mers

| D | $C_{25,d}$ | $Time_1$ | $SE2_d$ | $Time_2$ | X | PatMaN | Bowtie |
|---|---|---|---|---|---|---|---|
| 1 | 144 | 4.5 s | 1536 | 4.5 s | 1.0x | 106 s | 353 s |
| 2 | 64 | 7.5 s | 1536 | 4.5 s | 1.7x | 1080 s | 841 s |
| 3 | 32 | 15.0 s | 1008 | 6.8 s | 2.2x | >2 hr | 1731 s |
| 4 | 32 | 15.0 s | 672 | 9.8 s | 1.5x | >9 hr | — |
| 5 | 24 | 21.0 s | 480 | 12.8 s | 1.6x | — | — |

D: Hamming distance
$C_{25,d}$: # of traditional Hamming-dist automata (25, d) per core
$Time_1$: Solving time of traditional automata
$SE2_d$: # of 2-stride subset-encoded Hamming-dist automata per core
$Time_2$: Solving time of 2-stride subset-encoded automata
PatMaN, Bowtie: Solving time of PatMaN and Bowtie subset encoding technique is demonstrated for a 2-stride Hamming distance. The AP's execution time is estimated for matching 20,000 25-mers with 200 million DNA sequences in Table 3.

Since 64 DNA characters can be encoded into one STE using a $$\binom{4}{1}$$

encoding, and 25-mers are relatively short, they can not fully utilize all memory cells in each STE. Thus, using the subset encoding method, a tradeoff is made among input rate and the length of patterns that can be encoded into one STE. A 2-stride subset encoding, which maps pairs of DNA characters to subsets of $$\binom{16}{1}$$

is used. As a result, up to 256/16*2=32 characters can be encoded into one STE, and 2× input rate can be obtained at the same time.

The capacity and processing time of the AP are shown in Table 3. The AP processing time is calculated by 200 MB/133 MB/s×pass, where pass is the total number of 20,000 patterns divided by the number of patterns that can be placed on an AP board. Results show that the 2-stride subset-encoded Hamming distance automata can be up to 2.2× faster than traditional Hamming distance automata solutions.

The AP solution is more suitable for application scenarios, in which reference sequences are frequently changed, because it takes DNA reference sequence as input. For comparison, the single-threaded

TABLE 4

Compiling results of Levenshtein Automata

| Levenshtein | d = 1 | d = 2 | d = 3 | d = 4 |
|---|---|---|---|---|
| Traditional (64, d) | 24/core | 10/core | 6/core | failed |
| SE (64, d) | 1536/core | 288/core | 128/core | 48/core |
| SE (64, d) sliding | 24/core | 4.5/core | 2/core | 0.75/core | running times of two well-established CPU DNA aligning tools (PatMaN (Document 10) and Bowtie (Document 11)) are listed on this same problem.

Compiling Results for Levenshtein Automata

Traditional Levenshtein automata on the AP have very low STE utilization efficiency. According to the results from the Micron AP SDK compiler, 24 traditional instances of (64, 1) can be compiled in an AP core with 25.8% STE utilization, 10 instances of (64, 2) with 17.5% utilization, and 6 instances of (64, 3) with 13.3% utilization. In addition, on the current AP generation, the fan-in of each STE is bounded by 16. As a result, traditional Levenshtein automata for edit distance ≥4 fail to compile due to the intensive transitions caused by ε-transitions.

The subset-encoded Levenshtein automata mitigate this routing problem by factoring the large automaton structure into smaller pieces. Table 4 shows the compiling results of traditional Levenshtein automata versus the subset-encoded Levenshtein automata. It can be seen that the subset encoding method can provide capacity for up to 64× more Levenshtein automata for applications without sliding windows. It also makes edit distance d≥4 feasible on the AP, which was not possible to route using the traditional structure.

FUTURE APPLICABILITY

Technology Scaling of the AP

The current AP generation is based on 50 nm technology, while the state-of-the-art DRAM is using 20 nm technology, which is three generations ahead (37 nm, 25 nm, 20 nm). Thus, if the AP is normalized to the state-of-the-art semiconductor technology, and a 2× improvement is assumed

TABLE 5

Tradeoff between AP symbol size and the number of STEs

| c | 4 | 6 | 8 | 10 | 12 | 14 | 16 |
|---|---|---|---|---|---|---|---|
| n | 393216 | 98304 | 24576 | 6144 | 1536 | 384 | 96 |
| n' | 3145728 | 786432 | 196608 | 49152 | 12288 | 3072 | 768 | c: The symbol size of the AP
n: The number of STEs on one current AP core
n': The number of STEs on one AP core with 8× semiconductor technology scaling on capacity per node, 8× patterns can be placed on a future generation of the AP with 20 nm technology.

Impact on the Architecture of the AP

This new subset encoding technique brings up interesting considerations for the design of future AP architectures. There is a tradeoff between the native symbol size (i.e., how large the alphabet is) and the number of states. In Table 5, how the AP symbol size affects the number of STEs in one AP core is shown. The total number of memory cells is assumed to be constant, and two scenarios are considered: the current generation, and projecting an 8× increase in capacity after semiconductor technology scaling. Since Micron has not published details of its routing matrix, it is assumed that the fraction of area of the routing matrix is fixed. It can be seen from the table that small symbol sizes benefit applications with small alphabet size by providing more STEs, such as DNA applications. Large symbol sizes benefit applications that have larger alphabet sizes or long patterns without requiring sliding windows since they allow for a larger character set to be represented in one STE, and thus longer sequences by subset encoding. Note that the aspect ratio of the DRAM structures must also be taken into account. DRAM banks with high aspect ratios are not efficient, so the two ends of the scale in Table 5 may not be practical, because they would lead to very wide or very tall banks.

In addition, the subset encoding method can take advantage of the on-board FPGA for pre-processing or post-processing. The original data can be streamed in to the FPGA on the AP board, so that preprocessing the application data on CPU is not necessary.

Future Work

In the present invention, the subset encoding method and related automata designs for improving the pattern density on the Automata Processor are presented. The proposed method is a general method that can take advantage of the character-OR ability of STEs on the AP, and it relieves the problems of limited hardware capacity and inefficient routing. Experimental results show that after applying the subset encoding method on Hamming distance automata, up to 3.2× more patterns can be placed on the AP if sliding window is required, and 192× more if sliding window is not required. For Levenshtein distance, the subset encoding splits the Levenshtein automata into small chunks and makes them routable on the AP, allowing higher edit distance to be supported. In addition, the subset encoding method influences future decisions in the design of the AP or other automata-based co-processors. This idea of encoding sequences of data into subsets before doing NFA matching can also be applied to CPU (Central Processing Unit), GPU (Graphic Processing Unit) or FPGA (Field-Programmable Gate Array) regular expression matching implementations. By doing problem reductions, we may be able to utilize those hardware accelerators more efficiently.

Broad Scope of the Invention

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to."

In this disclosure and during the prosecution of this application, means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited.

In this disclosure and during the prosecution of this application, the terminology "present invention" or "invention" may be used as a reference to one or more aspect within the present disclosure. The language present invention or invention should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims.

In this disclosure and during the prosecution of this application, the terminology "embodiment" can be used to describe any aspect, feature, process or step, any combination thereof, and/or any portion thereof, etc. In some examples, various embodiments may include overlapping features. In this disclosure, the following abbreviated terminology may be employed: "e.g." which means "for example."

FIG. 19 is a block diagram that illustrates a system 130 including a computer system 140 and the associated Internet 11 connection upon which an embodiment, or a portion thereof, may be implemented. Such configuration is typically used for computers (hosts) connected to the Internet 11 and executing a server or a client (or a combination) software. A source computer such as laptop, an ultimate destination computer and relay servers, for example, as well as any computer or processor described herein, may use the computer system configuration and the Internet connection shown in FIG. 19. The system 140 may be used as a portable electronic device such as a notebook/laptop computer, a media player (e.g., MP3 based or video player), a cellular phone, a Personal Digital Assistant (PDA), an image processing device (e.g., a digital camera or video recorder), and/or any other handheld computing devices, or a combination of any of these devices. Note that while FIG. 19 illustrates various components of a computer system, it is not intended to represent any particular architecture or manner of interconnecting the components; as such details are not germane to the present invention. It will also be appreciated that network computers, hand-held computers, cell phones and other data processing systems which have fewer components or perhaps more components may also be used. The computer system of FIG. 19 may, for example, be an Apple Macintosh computer or Power Book, or an IBM compatible PC. Computer system 140 includes a bus 137, an interconnect, or other communication mechanism for communicating information, and a processor 138, commonly in the form of an integrated circuit, coupled with bus 137 for processing information and for executing the computer executable instructions. Computer system 140 also includes a main memory 134, such as a Random Access Memory (RAM) or other dynamic storage device, coupled to bus 137 for storing information and instructions to be executed by processor 138.

Main memory 134 also may be used for storing temporary variables or other intermediate information during execution of instructions to be executed by processor 138. Computer system 140 further includes a Read Only Memory (ROM) 136 (or other non-volatile memory) or other static storage device coupled to bus 137 for storing static information and instructions for processor 138. A storage device 135, such as a magnetic disk or optical disk, a hard disk drive for reading from and writing to a hard disk, a magnetic disk drive for reading from and writing to a magnetic disk, and/or an optical disk drive (such as DVD) for reading from and writing to a removable optical disk, is coupled to bus 137 for storing information and instructions. The hard disk drive, magnetic disk drive, and optical disk drive may be connected to the system bus by a hard disk drive interface, a magnetic disk drive interface, and an optical disk drive interface, respectively. The drives and their associated computer-readable media provide non-volatile storage of computer readable instructions, data structures, program modules and other data for the general purpose computing devices. Typically computer system 140 includes an Operating System (OS) stored in a non-volatile storage for managing the computer resources and provides the applications and programs with an access to the computer resources and interfaces. An operating system commonly processes system data and user input, and responds by allocating and managing tasks and internal system resources, such as controlling and allocating memory, prioritizing system requests, controlling input and output devices, facilitating networking and managing files. Non-limiting examples of operating systems are Microsoft Windows, Mac OS X, and Linux.

The term processor is meant to include any integrated circuit or other electronic device (or collection of devices) capable of performing an operation on at least one instruction including, without limitation, Reduced Instruction Set Core (RISC) processors, CISC microprocessors, Microcontroller Units (MCUs), CISC-based Central Processing Units (CPUs), and Digital Signal Processors (DSPs). The hardware of such devices may be integrated onto a single substrate (e.g., silicon die), or distributed among two or more substrates. Furthermore, various functional aspects of the processor may be implemented solely as software or firmware associated with the processor.

Computer system 140 may be coupled via bus 137 to a display 131, such as a Cathode Ray Tube (CRT), a Liquid Crystal Display (LCD), a flat screen monitor, a touch screen monitor or similar means for displaying text and graphical data to a user. The display may be connected via a video adapter for supporting the display. The display allows a user to view, enter, and/or edit information that is relevant to the operation of the system. An input device 132, including alphanumeric and other keys, is coupled to bus 137 for communicating information and command selections to processor 138. Another type of user input device is cursor control 133, such as a mouse, a trackball, or cursor direction keys for communicating direction information and command selections to processor 138 and for controlling cursor movement on display 131. This input device typically has two degrees of freedom in two axes, a first axis (e.g., x) and a second axis (e.g., y), that allows the device to specify positions in a plane.

The computer system 140 may be used for implementing the methods and techniques described herein. According to one embodiment, those methods and techniques are performed by computer system 140 in response to processor 138 executing one or more sequences of one or more instructions contained in main memory 134. Such instructions may be read into main memory 134 from another computer-readable medium, such as storage device 135. Execution of the sequences of instructions contained in main memory 134 causes processor 138 to perform the process steps described herein. In alternative embodiments, hard-wired circuitry may be used in place of or in combination with software instructions to implement the arrangement. Thus, embodiments of the invention are not limited to any specific combination of hardware circuitry and software. The term computer-readable medium (or machine-readable medium) as used herein is an extensible term that refers to any medium or any memory, that participates in providing instructions to a processor, (such as processor 138) for execution, or any mechanism for storing or transmitting information in a form readable by a machine (e.g., a computer). Such a medium may store computer-executable instructions to be executed by a processing element and/or control logic, and data which is manipulated by a processing element and/or control logic, and may take many forms, including but not limited to, non-volatile medium, volatile medium, and transmission medium. Transmission media includes coaxial cables, copper wire and fiber optics, including the wires that comprise bus 137. Transmission media can also take the form of acoustic or light waves, such as those generated during radio-wave and infrared data communications, or other form of propagated signals (e.g., carrier waves, infrared signals, digital signals, etc.). Common forms of computer-readable media include, for example, a floppy disk, a flexible disk, hard disk, magnetic tape, or any other magnetic medium, a CD-ROM, any other optical medium, punch-cards, paper-tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to processor 138 for execution. For example, the instructions may initially be carried on a magnetic disk of a remote computer. The remote computer can load the instructions into its dynamic memory and send the instructions over a telephone line using a modem. A modem local to computer system 140 can receive the data on the telephone line and use an infra-red transmitter to convert the data to an infra-red signal. An infra-red detector can receive the data carried in the infra-red signal and appropriate circuitry can place the data on bus 137. Bus 137 carries the data to main memory 134, from which processor 138 retrieves and executes the instructions. The instructions received by main memory 134 may optionally be stored on storage device 135 either before or after execution by processor 138.

Computer system 140 also includes a communication interface 141 coupled to bus 137. Communication interface 141 provides a two-way data communication coupling to a network link 139 that is connected to a local network 111. For example, communication interface 141 may be an Integrated Services Digital Network (ISDN) card or a modem to provide a data communication connection to a corresponding type of telephone line. As another non-limiting example, communication interface 141 may be a local area network (LAN) card to provide a data communication connection to a compatible LAN. For example, Ethernet based connection based on IEEE802.3 standard may be used such as 10/100 BaseT, 1000 BaseT (gigabit Ethernet), 10 gigabit Ethernet (10 GE or 10 GbE or 10 GigE per IEEE Std 802.3ae-2002 as standard), 40 Gigabit Ethernet (40 GbE), or 100 Gigabit Ethernet (100 GbE as per Ethernet standard IEEE P802.3ba), as described in Cisco Systems, Inc. Publication number 1-587005-001-3 (6/99), Internetworking Technologies Handbook, Chapter 7: Ethernet Technologies, pages 7-1 to 7-38, which is incorporated in its entirety for all purposes as if fully set forth herein. In such a case, the communication interface 141 typically include a LAN transceiver or a modem, such as Standard Microsystems Corporation SMSC) LAN91C111 10/100 Ethernet transceiver described in the Standard Microsystems Corporation (SMSC) data-sheet LAN91C111 10/100 Non-PCI Ethernet Single Chip MAC+PHY Data-Sheet, Rev. 15 (02-20-04), which is incorporated in its entirety for all purposes as if fully set forth herein. Wireless links may also be implemented. In any such implementation, communication interface 141 sends and receives electrical, electromagnetic or optical signals that carry digital data streams representing various types of information.

Network link 139 typically provides data communication through one or more networks to other data devices. For example, network link 139 may provide a connection through local network 111 to a host computer or to data equipment operated by an Internet Service Provider (ISP) 142. ISP 142 in turn provides data communication services through the world wide packet data communication network Internet 11. Local network 111 and Internet 11 both use electrical, electromagnetic or optical signals that carry digital data streams. The signals through the various networks and the signals on the network link 139 and through the communication interface 141, which carry the digital data to and from computer system 140, are exemplary forms of carrier waves transporting the information.

A received code may be executed by processor 138 as it is received, and/or stored in storage device 135, or other non-volatile storage for later execution. In this manner, computer system 140 may obtain application code in the form of a carrier wave.

Accordingly, an aspect of an embodiment provides, but not limited thereto, a system, method and computer readable medium for power pad placement of power delivery networks (PDN), which is important in, for example, computer-automated-design (CAD) of integrated circuits, and more particularly, the optimization of power pad locations and transient noise control. It should be appreciated that the related optimization system and method and the related networks, computer systems, internet, and components and functions may be implemented according to the scheme(s) disclosed herein.

Various embodiments or aspects of the invention, for example, can be implemented as software in a computing device, or alternatively, on hardware. An exemplary computing device in which an embodiment of the invention, or a portion thereof, can be implemented is schematically illustrated in FIGS. 20 and 21. Although some aspects may be known, a brief explanation will be provided herein for the convenience of other readers.

Referring to FIG. 20, in its most basic configuration, computing device 144 typically includes at least one processing unit 150 and memory 146. Depending on the exact configuration and type of computing device, memory 146 can be volatile (such as RAM), non-volatile (such as ROM, flash memory, etc.) or some combination of the two. Additionally, device 144 may also have other features and/or functionality. For example, the device could also include additional removable and/or non-removable storage including, but not limited to, magnetic or optical disks or tape, as well as writable electrical storage media. Such additional storage is the figure by removable storage 152 and non-removable storage 148. Computer storage media includes volatile and nonvolatile, removable and non-removable media implemented in any method or technology for storage of information such as computer readable instructions, data structures, program modules or other data. The memory, the removable storage and the non-removable storage are all examples of computer storage media. Computer storage media includes, but is not limited to, RAM, ROM, EEPROM, flash memory or other memory technology CDROM, digital versatile disks (DVD) or other optical storage, magnetic cassettes, magnetic tape, magnetic disk storage or other magnetic storage devices, or any other medium which can be used to store the desired information and which can accessed by the device. Any such computer storage media may be part of, or used in conjunction with, the device.

The device may also contain one or more communications connections 154 that allow the device to communicate with other devices (e.g. other computing devices). The communications connections carry information in a communication media. Communication media typically embodies computer readable instructions, data structures, program modules or other data in a modulated data signal such as a carrier wave or other transport mechanism and includes any information delivery media. The term modulated data signal means a signal that has one or more of its characteristics set or changed in such a manner as to encode, execute, or process information in the signal. By way of example, and not limitation, communication medium includes wired media such as a wired network or direct-wired connection, and wireless media such as radio, RF, infrared and other wireless media. As discussed above, the term computer readable media as used herein includes both storage media and communication media.

In addition to a stand-alone computing machine, embodiments of the invention can also be implemented on a network system comprising a plurality of computing devices that are in communication with a networking means, such as a network with an infrastructure or an ad hoc network. The network connection can be wired connections or wireless connections. As a way of example, FIG. 21 illustrates a network system in which embodiments of the invention can be implemented. In this example, the network system comprises computer 156 (e.g. a network server), network connection means 158 (e.g. wired and/or wireless connections), computer terminal 160, and PDA (e.g. a smart-phone) 162 (or other handheld or portable device, such as a cell phone, laptop computer, tablet computer, GPS receiver, mp3 player, handheld video player, pocket projector, etc. or handheld devices (or non portable devices) with combinations of such features). The embodiments of the invention can be implemented in anyone of the devices of the system. For example, execution of the instructions or other desired processing can be performed on the same computing device that is anyone of 156, 160, and 162. Alternatively, an embodiment of the invention can be performed on different computing devices of the network system. For example, certain desired or required processing or execution can be performed on one of the computing devices of the network (e.g. server 156), whereas other processing and execution of the instruction can be performed at another computing device (e.g. terminal 160) of the network system, or vice versa. In fact, certain processing or execution can be performed at one computing device (e.g. server 156); and the other processing or execution of the instructions can be performed at different computing devices that may or may not be networked. For example, the certain processing can be performed at terminal 160, while the other processing or instructions are passed to device 162 where the instructions are executed. This scenario may be of particular value especially when the PDA device, for example, accesses to the network through computer terminal 160 (or an access point in an ad hoc network). For another example, software to be protected can be executed, encoded or processed with one or more embodiments of the invention. The processed, encoded or executed software can then be distributed to customers. The distribution can be in a form of storage media (e.g. disk) or electronic copy.

Practice of an aspect of an embodiment (or embodiments) of the invention is presented herein for illustration only and should not be construed as limiting the invention in any way. An approach of the present invention systems and designs and optimization system and techniques may be based on the tools, programs and operating systems as discussed throughout this disclosure, such techniques can be applied to various hardware, tools, operating systems, virtual machine, PVM, or executable format.

It will be apparent to those skilled in the art that various modifications and variations can be made in the disclosed embodiments of the present invention without departing from the spirit or scope of the invention. Thus, it is intended that the present invention covers the modifications and variations of the embodiments disclosed above provided that they come within the scope of any claims and their equivalents.

What is claimed is:

1. An encoding method of a processor for a pattern matching application comprising the steps of:
    encoding a plurality of input data before streaming them into the processor,
    encoding and placing a plurality of patterns on loop structures on the processor, and
    matching the encoded input data on the processor using the loop structures,
    wherein the plurality of input data are application data, and the loop structures contain the encoded patterns, and
    wherein the processor is a non-von Neumann processor based on the architecture of a dynamic random-access memory (DRAM).

2. The encoding method according to claim 1, wherein both the plurality of input data and the plurality of patterns are encoded into subsets of characters.

3. The encoding method according to claim 1, wherein the encoded input data are put in a single self-loop state transition element (STE) or a loop structure with multiple STEs on the processor.

4. The encoding method according to claim 3, wherein the single self-loop STE or the loop structure with multiple STEs contains a set of characters.

5. The encoding method according to claim 4, wherein the looped STE structure remains activated when the set of characters in the looped STE structure and another set of characters streamed in serial are identical, and the looped STE structure is turned off when the set of characters in the looped STE structure and the another set of characters streamed in serial are not identical.

6. The encoding method according to claim 3, wherein an STE comprises an array of memory, and a value in the memory cell indicates whether the encoded input data matches with the encoded patterns on the processor.

7. The encoding method according to claim 6, wherein the processor further comprises a routing matrix for implementing connections among STEs, Boolean logic gates, and counters on the processor.

8. The encoding method according to claim 1, wherein the encoding and the matching are performed in parallel.

9. An automata design method of the processor for applying the encoding method according to claim 1 comprises:
    exact matching automata,
    Hamming distance automata,
    Levenshtein automata, and
    Damerau-Levenshtein automata.

SEQUENCE LISTING

<160> NUMBER OF SEQ ID NOS: 1

<210> SEQ ID NO 1
<211> LENGTH: 16
<212> TYPE: DNA
<213> ORGANISM: Artificial Sequence
<220> FEATURE:
<223> OTHER INFORMATION: Example data used in exact string matching

<400> SEQUENCE: 1
atgcatgtat tgaagt                                                    16

10. The automata design method according to claim 9, wherein in the exact matching automata, whether the plurality of input data and the plurality of patterns are exactly identical is determined.

11. The automata design method according to claim 9, wherein in the Hamming distance automata, an one-to-one encoding method, an one-to-many encoding method, a many-to-one encoding method, and a many-to-many encoding method are used.

12. The automata design method according to claim 9, wherein in the Hamming distance automata, a ladder structure with a predetermined level is constructed to match the plurality of input data with the plurality of patterns within a predetermined distance.

13. The automata design method according to claim 9, wherein the Hamming distance automata is used to match the plurality of input data and the plurality of patterns with sliding windows, and a size of the plurality of input data is larger than that of the plurality of patterns.

14. The automata design method according to claim 9, wherein in the Levenshtein automata, left-shifted and right-shifted encoding are used for capturing insertions and deletions.

15. The automata design method according to claim 9, wherein in the Damerau-Levenshtein automata, AND logic gates are used for capturing transpositions of adjacent characters.

* * * * *